(12) United States Patent
Pagé et al.

(10) Patent No.: US 7,550,495 B2
(45) Date of Patent: *Jun. 23, 2009

(54) COMPOUNDS, COMPOSITIONS CONTAINING THEM, PREPARATION THEREOF AND USES THEREOF I

(75) Inventors: Daniel Pagé, Québec (CA); Ziping Liu, Québec (CA); Maxime Tremblay, Québec (CA); Christopher Walpole, Québec (CA); Hua Yang, Québec (CA)

(73) Assignee: AstraZeneca AB, Sodertalje (SE)

( * ) Notice: Subject to any disclaimer, the term of this patent is extended or adjusted under 35 U.S.C. 154(b) by 42 days.

This patent is subject to a terminal disclaimer.

(21) Appl. No.: 11/419,603

(22) Filed: May 22, 2006

(65) Prior Publication Data

US 2006/0264490 A1    Nov. 23, 2006

Related U.S. Application Data

(63) Continuation of application No. PCT/SE2005/001403, filed on Sep. 22, 2005.

(60) Provisional application No. 60/640,306, filed on Dec. 30, 2004.

(30) Foreign Application Priority Data

Sep. 24, 2004    (WO) .............. PCT/GB2004/004124

(51) Int. Cl.
A61K 31/415    (2006.01)
C07D 235/08    (2006.01)
(52) U.S. Cl. .................... 514/394; 548/304.4
(58) Field of Classification Search .............. 548/304.4; 514/394
See application file for complete search history.

(56) References Cited

U.S. PATENT DOCUMENTS

| | | | |
|---|---|---|---|
| 5,482,956 A | 1/1996 | Lunkenheimer et al. | |
| 6,166,219 A | 12/2000 | Yamasaki et al. | |
| 6,348,032 B1 | 2/2002 | Sperl et al. | |
| 6,352,985 B1 | 3/2002 | Yamasaki et al. | |
| 6,376,515 B2 | 4/2002 | Zhu et al. | |
| 6,534,535 B1 | 3/2003 | Zhu et al. | |
| 6,632,815 B2 | 10/2003 | Zhu et al. | |
| 6,686,368 B1 | 2/2004 | Zhu et al. | |
| 6,720,317 B1 | 4/2004 | Song et al. | |
| 6,835,739 B2 | 12/2004 | Zhu et al. | |
| 6,844,367 B1 | 1/2005 | Zhu et al. | |
| 7,030,139 B2 | 4/2006 | Cheng et al. | |
| 7,115,645 B2 | 10/2006 | Halfbrodt et al. | |
| 2002/0006948 A1 | 1/2002 | Halfbrodt et al. | |
| 2002/0082280 A1 | 6/2002 | Sperl et al. | |
| 2004/0116465 A1 | 6/2004 | Cheng et al. | |
| 2006/0052421 A1 | 3/2006 | Welter et al. | |
| 2006/0094750 A1 | 5/2006 | Kon-I et al. | |
| 2007/0072853 A1 | 3/2007 | Liu et al. | |
| 2007/0082899 A1 | 4/2007 | Page et al. | |
| 2007/0225346 A1 | 9/2007 | Bohlin | |
| 2007/0244092 A1 | 10/2007 | Brown et al. | |

FOREIGN PATENT DOCUMENTS

| | | |
|---|---|---|
| EP | 0597304 B1 | 1/2001 |
| EP | 0583665 B1 | 3/2003 |
| EP | 1403255 A1 | 3/2004 |
| FR | 5354 M | 9/1967 |
| FR | 1604908 | 6/1972 |
| WO | 9411349 A1 | 5/1994 |
| WO | 9411350 A1 | 5/1994 |
| WO | 9724334 A1 | 7/1997 |
| WO | 0112600 A1 | 2/2001 |
| WO | 0119798 A2 | 3/2001 |
| WO | 0151473 | 7/2001 |
| WO | 0151473 A1 | 7/2001 |
| WO | 0200651 A2 | 1/2002 |
| WO | 0246168 A1 | 6/2002 |
| WO | 02085866 | 10/2002 |
| WO | 02085866 A1 | 10/2002 |
| WO | 2004085385 A2 | 10/2004 |
| WO | 2004108688 A1 | 12/2004 |
| WO | 2004108712 | 12/2004 |
| WO | 2004108712 A1 | 12/2004 |
| WO | 2005007625 A2 | 1/2005 |
| WO | 2005021547 | 3/2005 |
| WO | 2005021547 A2 | 3/2005 |
| WO | 2005030732 | 4/2005 |

(Continued)

OTHER PUBLICATIONS

Holenz Jorg et al., "Medicinal Chemistry Driven Approaches Toward Novel and Selective Serotonin 5-HT6 Receptor Ligands," J. Med. Chem. 2005, vol. 48, pp. 1781-1795, table 1, compound 16.

(Continued)

*Primary Examiner*—Rebecca L Anderson
(74) *Attorney, Agent, or Firm*—Jianzhong Shen

(57) ABSTRACT

Compounds of Formula I, or pharmaceutically acceptable salts thereof:

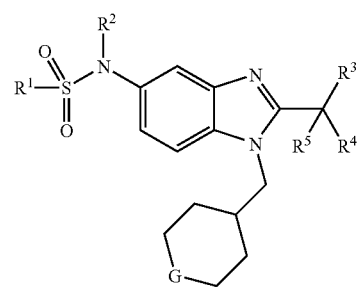

I wherein $R^1$, $R^2$, $R^3$, $R^4$, $R^5$, and G are as defined in the specification as well as salts and pharmaceutical compositions including the compounds are prepared. They are useful in therapy, in particular in the management of pain.

2 Claims, No Drawings

FOREIGN PATENT DOCUMENTS

| | | | |
|---|---|---|---|
| WO | 2005030732 | A1 | 4/2005 |
| WO | 2005030733 | | 4/2005 |
| WO | 2005030733 | A1 | 4/2005 |
| WO | 2005030761 | | 4/2005 |
| WO | 2005030761 | A1 | 4/2005 |
| WO | 2005030762 | A1 | 4/2005 |
| WO | 2005113542 | A2 | 12/2005 |
| WO | 2006009876 | A2 | 1/2006 |
| WO | 2006012642 | A2 | 2/2006 |
| WO | 2006033627 | A1 | 3/2006 |
| WO | 2006033628 | A1 | 3/2006 |
| WO | 2006033629 | A1 | 3/2006 |
| WO | 2006033630 | | 3/2006 |
| WO | 2006033630 | A1 | 3/2006 |
| WO | 2006033632 | A1 | 3/2006 |
| WO | 2006033633 | | 3/2006 |
| WO | 2006033633 | A1 | 3/2006 |
| WO | 2006048754 | A1 | 5/2006 |
| WO | 2006078941 | A2 | 7/2006 |
| WO | 2007108754 | A1 | 9/2007 |
| WO | 2007120101 | A1 | 10/2007 |

OTHER PUBLICATIONS

Restriction Requirement issued for U.S. Appl. No. 11/689,864 on Mar. 24, 2008.
Final Rejection issued for U.S. Appl. No. 11/689,864 on Jan. 8, 2009.
Chawla et al., "Challenges in Polymorphism of Pharmaceuticals," Crips, vol. 5(1), Jan.-Mar. 2004, pp. 9-12.
Newman et al., "Solid-state analysis of the active pharmaceutical ingredient in drug products," Drug Discovery Today, vol. 8(19), Oct. 2003, pp. 898-905.
Evans et al., "Synthesis of a group of 1H-benzimidazoles and their screening for antiinflammatory activity," Eur J Med Chem, 1996, vol. 31, pp. 635-642, example 27.
Holenz et al., "Medicinal chemistry driven approaches toward novel and selective serotonin 5-HT6 receptor ligands," J. Med. Chem., 2005, vol. 48, pp. 1781-1795, table 1, compound 16, abstract.
Li et al., "Benzimidazole derivatives as novel nonpeptide luteinizing hormone-releasing hormone (LHRH) antagonists. Part 2: Benzimidazole-5-sulfonamides," Bioorganic & Medicinal Chemistry Letters, 2005, 15(3), pp. 805-807.
STN International, File CAPLUS, accession No. 1972:419030, doc. No. 77:19030, Koshienko et al., "Benzo(1,2-d:3,4-d')diimidazole derivatives. II. Behavior of 3,6-dimethyl-and 3,6,7-trimethylbenzo(1,2-d:3,4-d')diimidazole toward nucleophilic agents," Khimiya Geterotsiklicheskikh Soedinenii, 1971, 7(8), pp. 1132-1135; XP002307925.
STN Intnl, File CHEMCATS, access No. 2003:1839419, "Benzenesulfonamide, N-(1,2-dimethyl-1H-benzimidazol-5-yl)-", CAS Reg No. 488708-12-9; & STN Intnl, File CHEMCATS, access No. 2003:2399372, "Benzenesulfonamide, N-(2-methyl-1-(phenylmethyl)-1H-benzimidazol-5-yl-", CAS Registry No. 488841-64-1; & STN Intnl, File CHEMCATS, access No. 2003:2595844, "Benzenesulfonamide, 4-methyl-N-(2-methyl-1-(phenylmethyl)-1H-benzimidazole-5-yl)-", CAS Reg. No. 312617-94-0, 2002.
STN Intnl, File CHEMCATS, accession No. 2003:1839419, "Benzenesulfonamide, N-(1,2-dimethyl-1H-benzimidazol-5-yl)-" CAS Registry No. 488708-12-9; & STN Intnl, File CHEMCATS, accession No. 2003:1845322, "Benzenesulfonamide, 4-bromo-N-(1,2-dimethyl-1H-benzimidal-5-yl)-", CAS Registry No. 489397-82-2; & STN Intnl. File CHEMCATS, accession No. 2003:2305521, "Benzenesulfonamide, N-(1,2-dimethyl-1H-benzimidazol-5-yl)-1-fluoro-", CAS Registry No. 503429-33-2, 2002.
STN Intnl, file Registry, see RN: 848855-83-4, 2005.
STN Intnl, File CAPLUS, accession No. 1975:408737, doc No. 83:8737, Bieksa, V. et al., "Relation of the reactivity of chloroethyl derivatives of 3,4-diaminobenzenesulfopiperidides to the structure of alkylating group", Lietuvos TSR Mokslu Akademijos Darbai, Serija B: Chemija, Technika, Fizine Geografija, (1974), (3) 91-8.
STN Intnl, File CAPLUS, accession No. 1973:515496, doc No. 79:115496, Bieksa, V. et al. "Chloroalkyl derivatives of benzimidazoles. 1. Chloroethyl derivatives of 2-methylbenzimidazole-5-sulfonamide," Lietuvos TSR Mokslu Akademijos Darbai, Serija B: Chemija, Technika, Fizine Geografija, (1973), (2), 93-103.
ISR issued for PCT/SE2005/001403 on Dec. 14, 2005.
English abstract for EP 0597304, 2001.
English abstract for FR 1604908, 1972.
English abstract for FR 5354M, 1967.
English abstract for WO 9411349, 1994.
English abstract for WO 9411350, 1994.
English abstract for WO 9724334, 1997.
English abstract for WO 0151473, 2001.
Non-Final Office Action issued for U.S. Appl. No. 11/689,864 on Jul. 9, 2008.
Brittain et al., "Effects of Pharmaceutical Processing on Drug Polymorphs and Solvates," Polymorphism in Pharmaceutical Solids, vol. 95, pp. 331-361, 1999.
Express-Pharma-Online (http://www.expresspharmaonline.com/20031023/edit02.shtml) 2003.
Notice of Allowance issued for U.S. Appl. No. 11/689,864 on Apr. 10, 2009; AZ Ref. 102218-2 US.

COMPOUNDS, COMPOSITIONS CONTAINING THEM, PREPARATION THEREOF AND USES THEREOF I

CROSS-REFERENCE TO RELATED APPLICATIONS

This application is a Continuation of International Application No. PCT/SE2005/001403, filed on Sep. 22, 2005. The international application claims priority under 35 U.S.C. 119(e) to U.S. Provisional Application No. 60/640,306, filed on Dec. 30, 2004 and claims priority under 35 U.S.C. 119(a)-(d) to International Application No. PCT/GB2004/004124, filed on Sep. 24, 2004.

BACKGROUND OF THE INVENTION

1. Field of the Invention

The invention is related to therapeutic compounds, pharmaceutical compositions containing these compounds, manufacturing processes thereof and uses thereof. Particularly, the present invention is related to compounds that may be effective in treating pain, cancer, multiple sclerosis, Parkinson's disease, Huntington's chorea, Alzheimer's disease, anxiety disorders, gastrointestinal disorders and/or cardiovascular disorders.

2. Discussion of Relevant Technology

Pain management has been studied for many years. It is known that cannabinoid receptor (e.g., $CB_1$ receptor, $CB_2$ receptor) ligands including agonists, antagonists and inverse agonists produce relief of pain in a variety of animal models by interacting with $CB_1$ and/or $CB_2$ receptors. Generally, $CB_1$ receptors are located predominately in the central nervous system, whereas $CB_2$ receptors are located primarily in the periphery and are primarily restricted to the cells and tissues derived from the immune system.

While $CB_1$ receptor agonists, such as $\Delta^9$-tetrahydrocannabinol ($\Delta^9$-THC) and anadamide, are useful in anti-nociception models in animals, they tend to exert undesired CNS side-effects, e.g., psychoactive side effects, the abuse potential, drug dependence and tolerance, etc. These undesired side effects are known to be mediated by the $CB_1$ receptors located in CNS. There are lines of evidence, however, suggesting that $CB_1$ agonists acting at peripheral sites or with limited CNS exposure can manage pain in humans or animals with much improved overall in vivo profile.

Therefore, there is a need for new $CB_1$ receptor ligands such as agonists that may be useful in managing pain or treating other related symptoms or diseases with reduced or minimal undesirable CNS side-effects.

DESCRIPTION OF THE EMBODIMENTS

The present invention provides $CB_1$ receptor ligands which may be useful in treating pain and/or other related symptoms or diseases.

The term "$C_{m-n}$" or "$C_{m-n}$ group" used alone or as a prefix, refers to any group having m to n carbon atoms.

The term "alkyl" used alone or as a suffix or prefix, refers to a saturated monovalent straight or branched chain hydrocarbon radical comprising 1 to about 12 carbon atoms. Illustrative examples of alkyls include, but are not limited to, $C_{1-4}$alkyl groups, such as methyl, ethyl, propyl, isopropyl, 2-methyl-1-propyl, 2-methyl-2-propyl, butyl, isobutyl, t-butyl.

The term "cycloalkyl," used alone or as suffix or prefix, refers to a saturated monovalent ring-containing hydrocarbon radical comprising at least 3 up to about 12 carbon atoms. Examples of cycloalkyls include, but are not limited to, $C_{3-7}$cycloalkyl groups, such as cyclopropyl, cyclobutyl, cyclopentyl, cyclohexyl, and cycloheptyl, and saturated cyclic and bicyclic terpenes. A cycloalkyl can be unsubstituted or substituted by one or two suitable substituents. Preferably, the cycloalkyl is a monocyclic ring or bicyclic ring.

The term "alkoxy" used alone or as a suffix or prefix, refers to radicals of the general formula —O—R, wherein R is an alkyl. Exemplary alkoxy includes methoxy, ethoxy, propoxy, isopropoxy, butoxy, t-butoxy, and isobutoxy.

Halogen includes fluorine, chlorine, bromine and iodine.

"RT" or "rt" means room temperature.

In one aspect, an embodiment of the invention provides a compound of Formula I, a pharmaceutically acceptable salt thereof, diastereomers, enantiomers, or mixtures thereof:

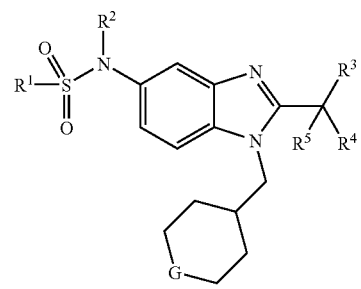

I wherein
G is selected from —O—, —CHF— and —$CF_2$—;
$R^1$ is selected from $C_{1-6}$alkyl and $C_{3-6}$cycloalkyl;
$R^2$ is selected from —H and methyl; and
$R^3$, $R^4$ and $R^5$ are independently selected from fluoro and methyl.

In another embodiment, the compounds may be those of formula I, wherein
G is selected from —O— and —$CF_2$—;
$R^1$ is selected from $C_{1-6}$alkyl and $C_{3-6}$cycloalkyl;
$R^2$ is selected from —H and methyl; and
$R^3$, $R^4$ and $R^5$ are independently selected from fluoro and methyl.

Another embodiment of the invention provides a compound of formula I, wherein
G is selected from —O— and —$CF_2$—;
$R^1$ is selected from $C_{1-4}$alkyl and $C_{3-4}$cycloalkyl;
$R^2$ selected from —H and methyl; and
$R^3$, $R^4$ and $R^5$ are independently selected from fluoro and methyl.

A further embodiment of the invention provides a compound of formula I, wherein
G is —O—;
$R^1$ is selected from ethyl, propyl and cyclopropyl;
$R^2$ selected from —H and methyl; and
$R^3$, $R^4$ and $R^5$ are independently selected from fluoro and methyl with $R^3$, $R^4$ and $R^5$ being the same.

An even further embodiment of the invention provides a compound of formula I, wherein
G is —$CF_2$—;
$R^1$ is selected from ethyl, propyl and cyclopropyl;

$R^2$ selected from —H and methyl; and
$R^3$, $R^4$ and $R^5$ are independently selected from fluoro and methyl with $R^3$, $R^4$ and $R^5$ being the same.

An even further embodiment of the invention provides a compound of formula I,
wherein
  G is —CHF—;
  $R^1$ is selected from ethyl, propyl, t-butyl and cyclopropyl;
  $R^2$ selected from —H and methyl; and
  $R^3$, $R^4$ and $R^5$ are independently selected from fluoro and methyl with $R^3$, $R^4$ and $R^5$ being the same.

In another embodiment, $R^1$ of formula I is selected from ethyl, propyl, t-butyl and cyclopropyl.

In another embodiment, G of formula I is —CHF— or —CF$_2$—.

In another embodiment, $R^3$, $R^4$ and $R^5$ of formula I are selected from fluoro and methyl with $R^3$, $R^4$ and $R^5$ being the same.

In another embodiment, the compound of the invention may be selected from N-[2-tert-Butyl-1-(tetrahydro-2H-pyran-4-ylmethyl)-1H-benzimidazol-5-yl]-N-methylcyclopropanesulfonamide;
N-[2-tert-Butyl-1-(tetrahydro-2H-pyran-4-ylmethyl)-1H-benzimidazol-5-yl]-N-methylpropane-1-sulfonamide;
N-[2-tert-Butyl-1-(tetrahydro-2H-pyran-4-ylmethyl)-1H-benzimidazol-5-yl]-N-methylbutane-1-sulfonamide;
N-{2-tert-Butyl-1-[(4,4-difluorocyclohexyl)methyl]-1H-benzimidazol-5-yl}-N-methylbutane-1-sulfonamide;
N-methyl-N-[1-(tetrahydro-2H-pyran-4-ylmethyl)-2-(trifluoromethyl)-1H-benzimidazol-5-yl]propane-1-sulfonamide;
N-methyl-N-[1-(tetrahydro-2H-pyran-4-ylmethyl)-2-(trifluoromethyl)-1H-benzimidazol-5-yl]cyclopropanesulfonamide;
N-[2-tert-Butyl-1-(tetrahydro-2H-pyran-4-ylmethyl)-1H-benzimidazol-5-yl]-N-methylpentane-1-sulfonamide;
N-[2-tert-Butyl-1-(tetrahydro-2H-pyran-4-ylmethyl)-1H-benzimidazol-5-yl]-N-methylethanesulfonamide;
N-[2-tert-Butyl-1-(tetrahydro-2H-pyran-4-ylmethyl)-1H-benzimidazol-5-yl]-N,2-dimethylpropane-2-sulfonamide;
N-{2-tert-Butyl-1-[(4,4-difluorocyclohexyl)methyl]-1H-benzimidazol-5-yl}-N-methylpropane-1-sulfonamide;
N-{2-tert-Butyl-1-[(4,4-difluorocyclohexyl)methyl]-1H-benzimidazol-5-yl}-N-methylethanesulfonamide;
N-{2-tert-Butyl-1-[(4,4-difluorocyclohexyl)methyl]-1H-benzimidazol-5-yl}propane-1-sulfonamide;
N-{2-tert-Butyl-1-[(4,4-difluorocyclohexyl)methyl]-1H-benzimidazol-5-yl}methanesulfonamide;
N-{2-tert-Butyl-1-[(4,4-difluorocyclohexyl)methyl]-1H-benzimidazol-5-yl}ethanesulfonamide;
N-{2-tert-Butyl-1-[(4,4-difluorocyclohexyl)methyl]-1H-benzimidazol-5-yl}cyclopropanesulfonamide;
N-{2-tert-Butyl-1-[(4,4-difluorocyclohexyl)methyl]-1H-benzimidazol-5-yl}-N-methylcyclopropanesulfonamide;
N-{2-tert-Butyl-1-[(4,4-difluorocyclohexyl)methyl]-1H-benzimidazol-5-yl}-2-methylpropane-2-sulfonamide;
N-[1-[(4,4-Difluorocyclohexyl)methyl]-2-(1,1-difluoroethyl)-1H-benzimidazol-5-yl]cyclopropanesulfonamide;
N-[1-[(4,4-Difluorocyclohexyl)methyl]-2-(1,1-difluoroethyl)-1H-benzimidazol-5-yl]ethanesulfonamide;
N-[1-[(4,4-Difluorocyclohexyl)methyl]-2-(1,1-difluoroethyl)-1H-benzimidazol-5-yl]-2-methylpropane-2-sulfonamide;
N-[2-(1,1-difluoroethyl)-1-(tetrahydro-2H-pyran-4-ylmethyl)-1H-benzimidazol-5-yl]-N-methylethanesulfonamide;
N-[2-(1,1-difluoroethyl)-1-(tetrahydro-2H-pyran-4-ylmethyl)-1H-benzimidazol-5-yl]-N-methylpropane-1-sulfonamide;
N-[2-(1,1-difluoroethyl)-1-(tetrahydro-2H-pyran-4-ylmethyl)-1H-benzimidazol-5-yl]-N-methylcyclopropanesulfonamide;
N-{2-tert-Butyl-1-[(4-fluorocyclohexyl)methyl]-1H-benzimidazol-5-yl}ethanesulfonamide;
N-{2-tert-Butyl-1-[(4-fluorocyclohexyl)methyl]-1H-benzimidazol-5-yl}cyclopropanesulfonamide;
N-{2-tert-Butyl-1-[(4-fluorocyclohexyl)methyl]-1H-benzimidazol-5-yl}-2-methylpropane-2-sulfonamide;

and pharmaceutically acceptable salts thereof.

A further embodiment of the invention provides a compound selected from

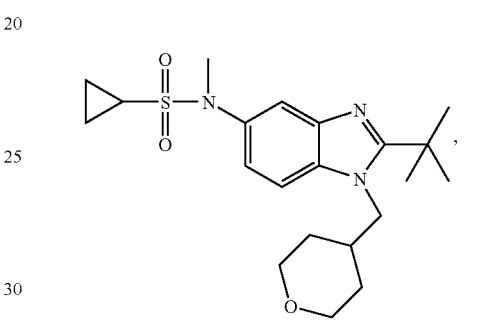

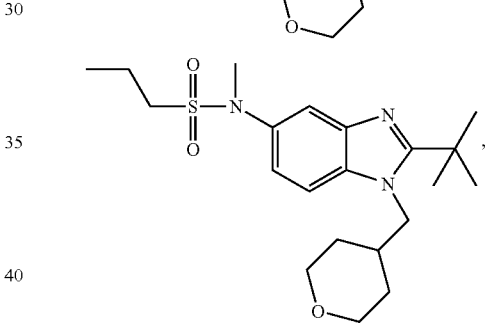

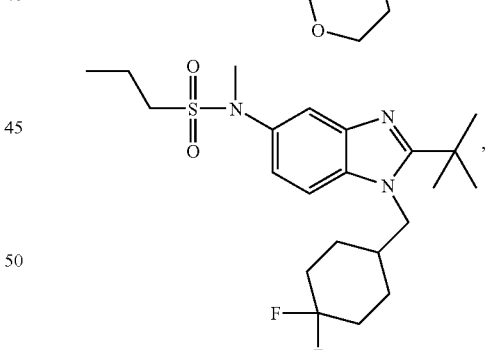

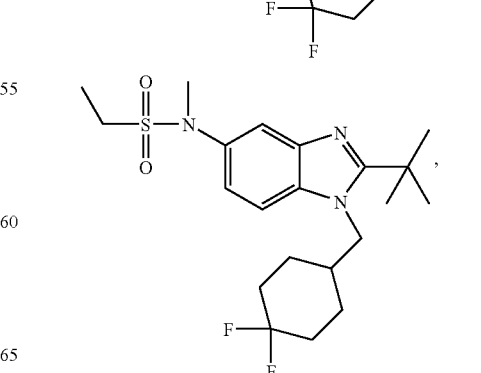

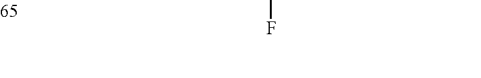

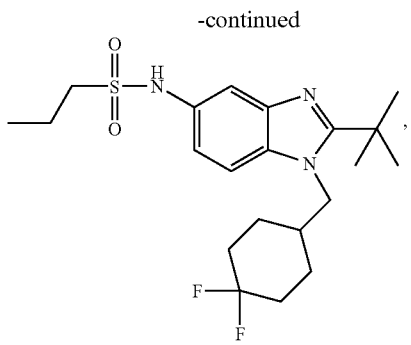

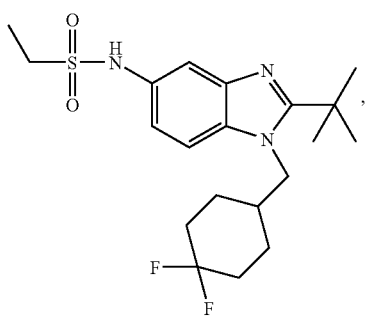

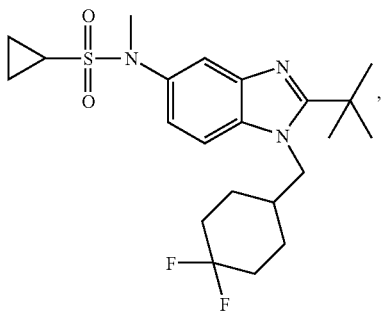

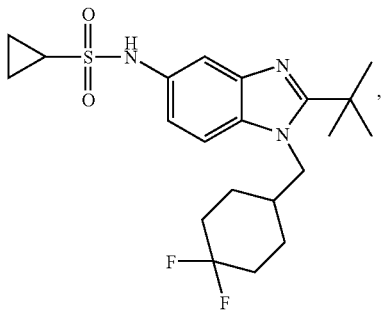

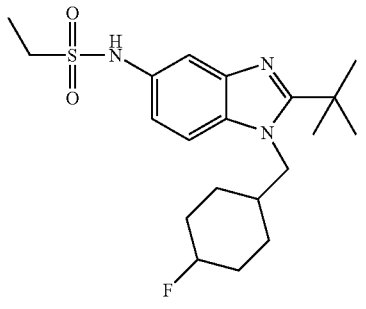

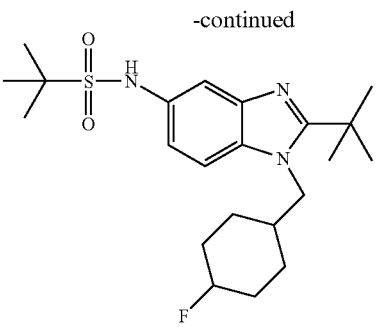

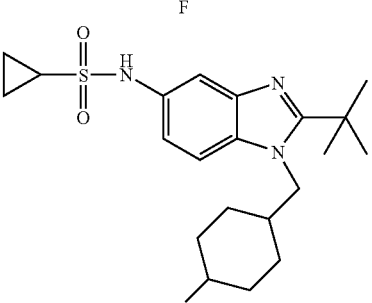

and pharmaceutically acceptable salts thereof

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the Formula I.

It will also be understood that certain compounds of the present invention may exist in solvated, for example hydrated, as well as unsolvated forms. It will further be understood that the present invention encompasses all such solvated forms of the compounds of the Formula I.

Within the scope of the invention are also salts of the compounds of the Formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of Formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have now found that the compounds of the invention have activity as pharmaceuticals, in particular as modulators or ligands such as agonists, partial agonists, inverse agonist or antagonists of $CB_1$ receptors. More particularly, the compounds of the invention exhibit selective activity as agonist of the $CB_1$ receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of $CB_1$ receptors is present or implicated. Furthermore, the compounds of the invention may be used to treat cancer, multiple sclerosis, Parkinson's disease, Huntington's chorea, Alzheimer's disease, anxiety disorders, gastrointestinal disorders and cardiovascular disorders.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of cannabinoid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the Formula I above, for the manufacture of a medicament for the treatment of any of the conditions discussed above.

A further aspect of the invention is a method for the treatment of a subject suffering from any of the conditions discussed above, whereby an effective amount of a compound according to the Formula I above, is administered to a patient in need of such treatment.

Thus, the invention provides a compound of Formula I or pharmaceutically acceptable salt or solvate thereof, as hereinbefore defined for use in therapy.

In a further aspect, the present invention provides the use of a compound of Formula I or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, transdermally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (per cent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of Formula I as defined above for the manufacture of a medicament.

Also within the scope of the invention is the use of any compound of Formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the Formula I above, is administered to a patient in need of such therapy.

Additionally, there is provided a pharmaceutical composition comprising a compound of Formula I or a pharmaceutically acceptable salt thereof, in association with a pharmaceutically acceptable carrier.

Particularly, there is provided a pharmaceutical composition comprising a compound of Formula I or a pharmaceutically acceptable salt thereof, in association with a pharmaceutically acceptable carrier for therapy, more particularly for therapy of pain.

Further, there is provided a pharmaceutical composition comprising a compound of Formula I or a pharmaceutically acceptable salt thereof, in association with a pharmaceutically acceptable carrier use in any of the conditions discussed above.

In a further aspect, the present invention provides a method of preparing the compounds of the present invention.

In one embodiment, the invention provides a process for preparing a compound of Formula I, comprising:

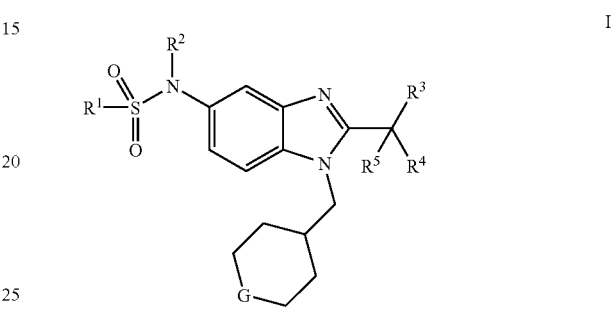

reacting a compound of Formula II with a compound of formula III,

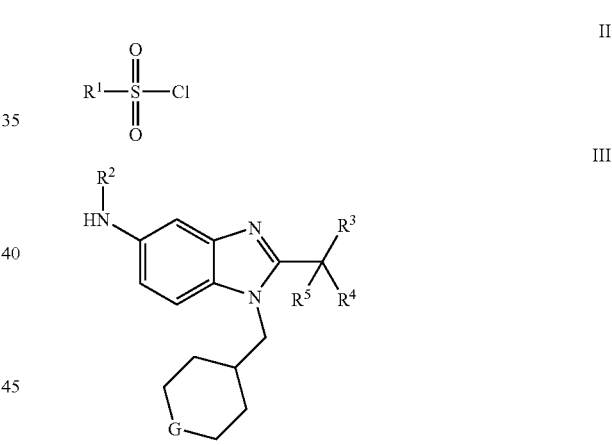

wherein $R^1$, $R^2$, $R^3$, $R^4$, $R^5$ and G are as defined above.

Compounds of the present invention may also be prepared according to the synthetic routes as depicted in Schemes 1, 2 and 3.

Scheme 1

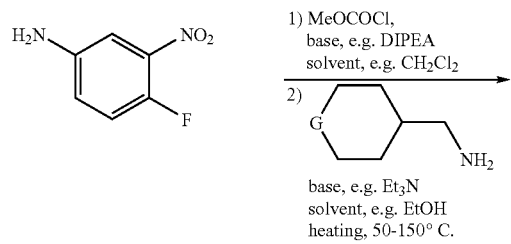

1) MeOCOCl,
base, e.g. DIPEA
solvent, e.g. $CH_2Cl_2$

2)

base, e.g. $Et_3N$
solvent, e.g. EtOH
heating, 50-150° C.

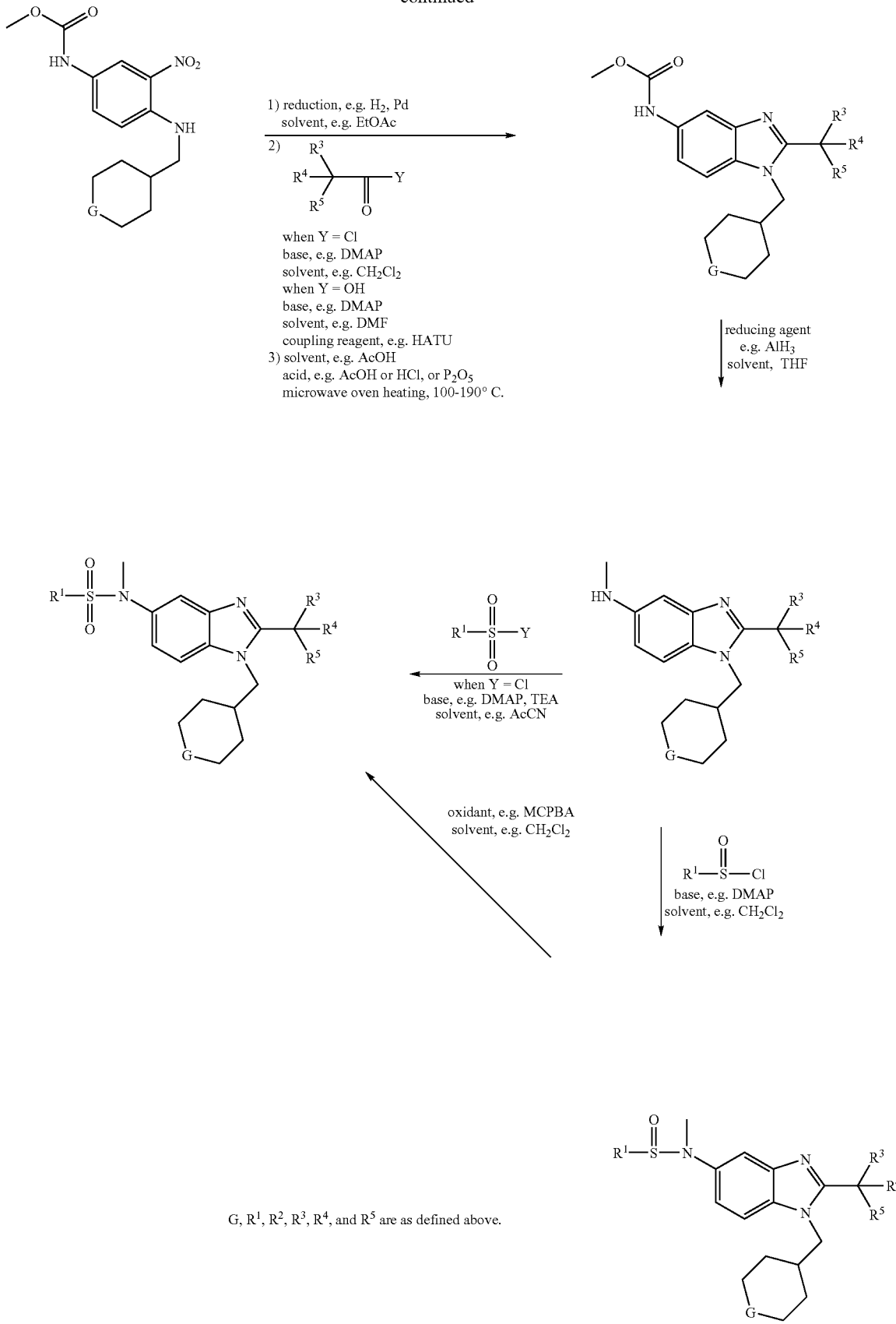

-continued when Y = Cl
base, e.g. DMAP
solvent, e.g. CH$_2$Cl$_2$
when Y = OH
base, e.g. DMAP
solvent, e.g. DMF
coupling reagent, e.g. HATU
3) solvent, e.g. AcOH
acid, e.g. AcOH or HCl, or P$_2$O$_5$
microwave oven heating, 100-190° C.

reducing agent
e.g. AlH$_3$
solvent, THF when Y = Cl
base, e.g. DMAP, TEA
solvent, e.g. AcCN oxidant, e.g. MCPBA
solvent, e.g. CH$_2$Cl$_2$ base, e.g. DMAP
solvent, e.g. CH$_2$Cl$_2$ G, R$^1$, R$^2$, R$^3$, R$^4$, and R$^5$ are as defined above.

Scheme 2
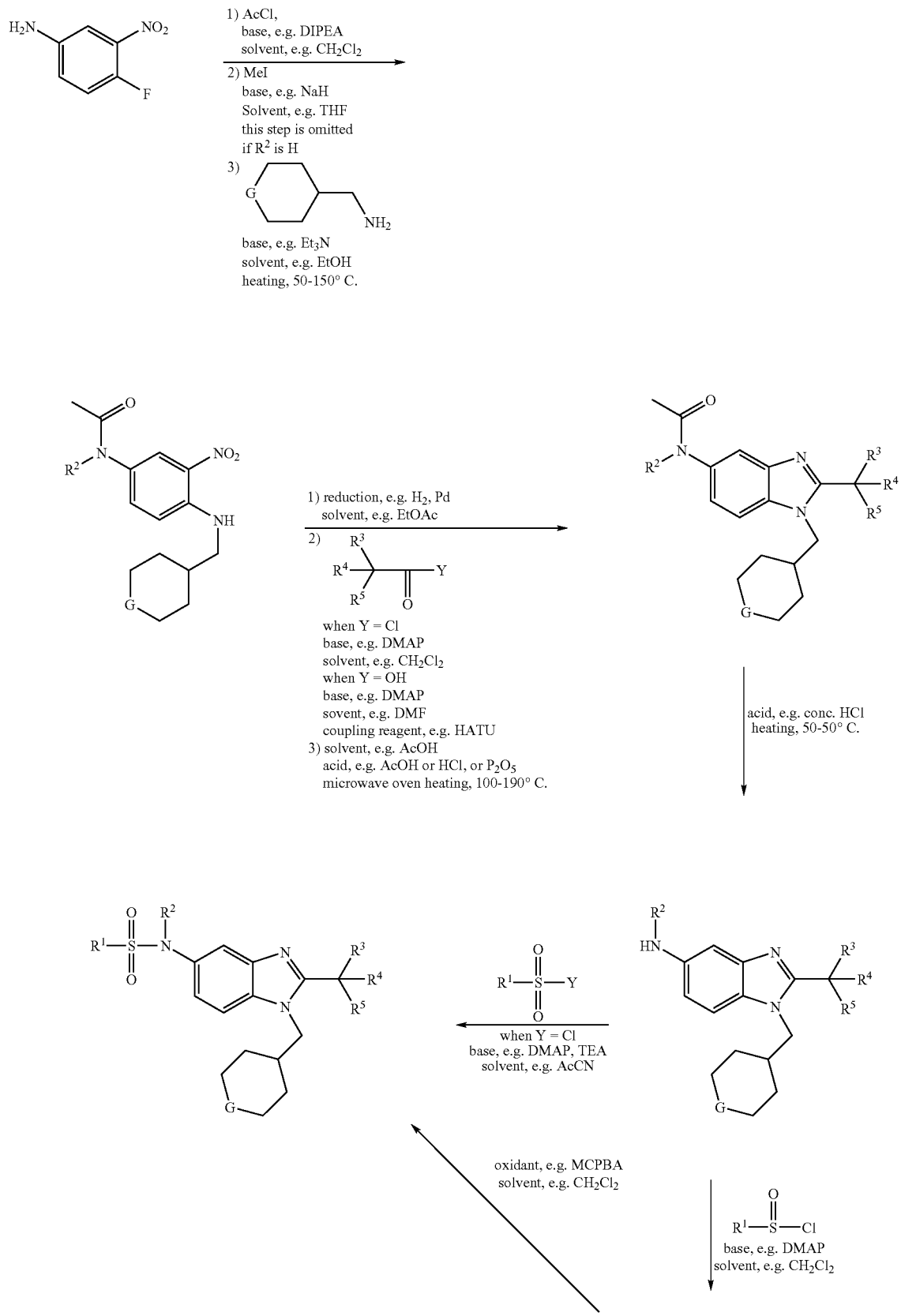

-continued

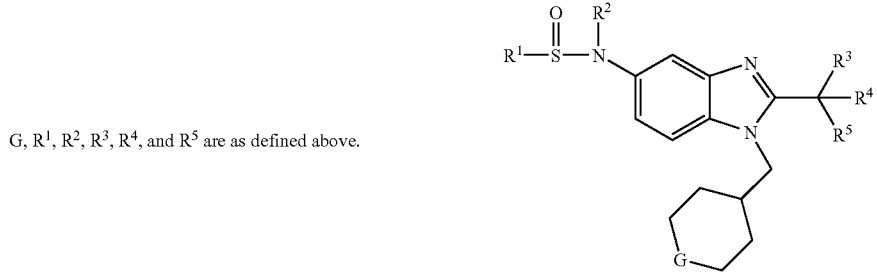

G, $R^1$, $R^2$, $R^3$, $R^4$, and $R^5$ are as defined above.

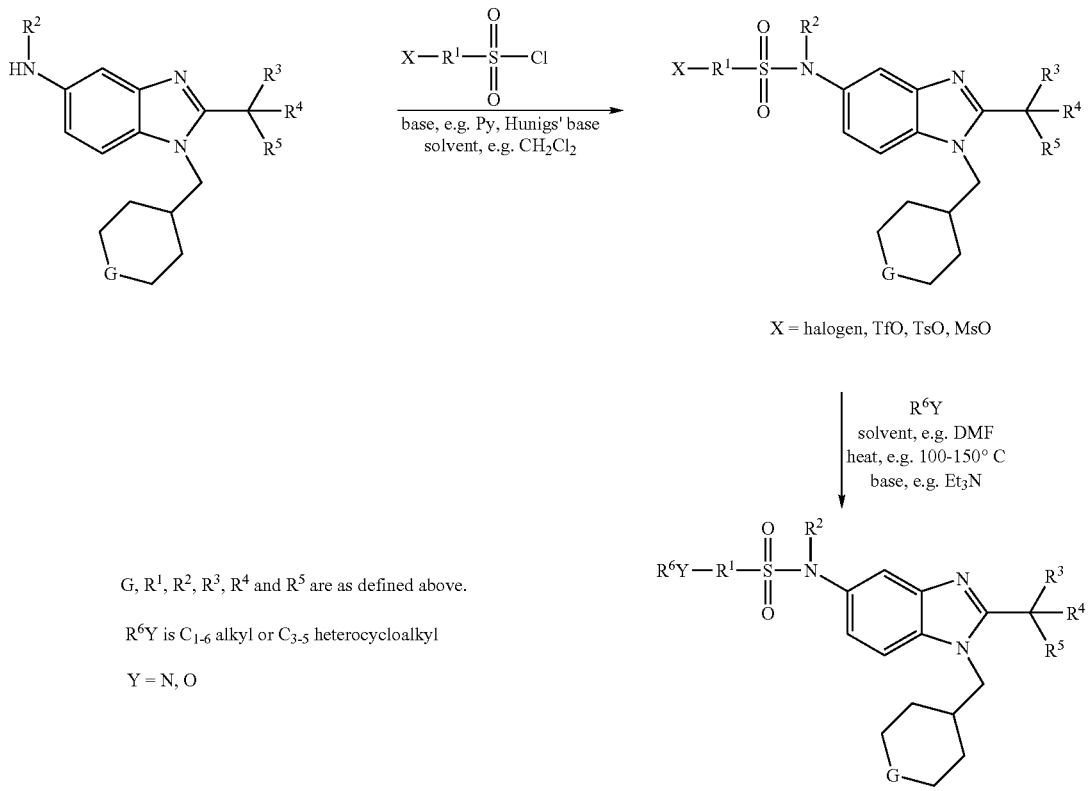

G, $R^1$, $R^2$, $R^3$, $R^4$ and $R^5$ are as defined above.

$R^6Y$ is $C_{1-6}$ alkyl or $C_{3-5}$ heterocycloalkyl

Y = N, O

Biological Evaluation hCB$_1$ and hCB$_2$ Receptor Binding

Human CB$_1$ receptor from Receptor Biology (hCB$_1$) or human CB$_2$ receptor from BioSignal (hCB$_2$) membranes are thawed at 37° C., passed 3 times through a 25-gauge blunt-end needle, diluted in the cannabinoid binding buffer (50 mM Tris, 2.5 mM EDTA, 5 mM MgCl$_2$, and 0.5 mg/mL BSA fatty acid free, pH 7.4) and aliquots containing the appropriate amount of protein are distributed in 96-well plates. The IC$_{50}$ of the compounds of the invention at hCB$_1$ and hCB$_2$ are evaluated from 10-point dose-response curves done with $^3$H-CP55,940 at 20000 to 25000 dpm per well (0.17-0.21 nM) in a final volume of 300 μl. The total and non-specific binding are determined in the absence and presence of 0.2 μM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM MgCl$_2$, 0.5 mg BSA pH 7.0). The filters are dried for 1 hour at 55° C. The radioactivity (cpm) is counted in a TopCount (Packard) after adding 65 μl/well of MS-20 scintillation liquid.

hCB$_1$ and hCB$_2$ GTPγS Binding

Human CB$_1$ receptor from Receptor Biology (hCB$_1$) or human CB$_2$ receptor membranes (BioSignal) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM MgCl$_2$, pH 7.4, 0.1% BSA). The EC$_{50}$ and E$_{max}$ of the compounds of the invention are evaluated from 10-point dose-response curves done in 300 μl with the appropriate amount of membrane protein and 100000-130000 dpm of GTPg$^{35}$S per well (0.11-0.14 nM). The basal and maximal stimulated binding is determined in absence and presence of 1 μM (hCB$_2$) or 10 μM (hCB$_1$) Win 55,212-2 respectively. The membranes are pre-incubated for 5 minutes with 56.25 μM (hCB2) or 112.5 μM (hCB$_1$) GDP prior to distribution in plates (15 µM (hCB$_2$) or 30 µM (hCB$_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM MgCl$_2$, 50 mM NaCl, pH 7.0). The filters are dried for 1 hour at 55° C. The radioactivity (cpm) is counted in a TopCount (Packard) after adding 65 µl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki = IC_{50}/(1+[rad]/Kd),$$

Wherein IC$_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Using the above-mentioned assays, the Ki towards human CB$_1$ receptors for certain compounds of the invention are in the range of between 3 nM and 195 nM. EC$_{50}$ for these compounds are in the range of between 2.3 nM and 300 nM. Emax for these compounds are in the range of between 109% and 144%.

Assay Condition for Measuring Solubility

A 30 mM DMSO stock is prepared of the sample and then a 25 µL aliquot is added to a 96-well plate and genevac at 40° C. for 4 hours. To the genevac compound add 250 µL of sodium phosphate buffer (pH 7.4) and then mix at 1200 rpm for 24 h using an Eppendorf Thermomixer at 25° C. After mixing solution is transferred to a 96-well Whatman GF/B filter plate and then filtered under vacuum. The supernatant is then injected onto the LC/MS for analysis and quantitation is performed using a 1-point calibration for the compound of interest.

Metabolic Stability Assays in Rat and Human Liver Microsomes

A solution of 500 µl of 100 µM compound in DMSO is incubated with human or rat liver microsomes (843 µl of microsomes of 0.5618 mg/mL in 30 ml 0.1 M KH$_2$PO$_4$ buffer pH7.4) at 37° C. for 10 min in a 96-deep well plate. NADPH (46 µL) at a concentration of 8.33 mg/ml in 100 mM KH$_2$PO$_4$ buffer pH 7.4 is added to start the reaction. The reaction mixtures are transferred to a 384-well plate containing acetonitrile to quench the reaction at time 0, 10, 20, 30 minutes. The 384 well plate is centrifuged for 30 min at 9000 g, at 4° C., from which samples are analyzed by LC/MS (model: XDB Eclipse C18). Three references are analyzed by LC/MS as a positive control. Data are processed following a standard procedure. The metabolic stability of assayed compounds is expressed as µL/min/mg In addition, metabolic stabilities (hClint and rClint) and soluabilities (aqueous) of selected compounds of the invention are determined using one or more assays described above. It is found that the selected compounds have improved metabolic stabilities and/or soluabilities in water. The metabolic stabilities and soluabilities for these selected compounds are illustrated in Table 1 below.

TABLE 1

Metabolic stabilities (hClint and rClint) and soluabilities:

| | Solubility (M) | hCLint (ul/min/mg) | rCLint (ul/min/mg) |
|---|---|---|---|
| 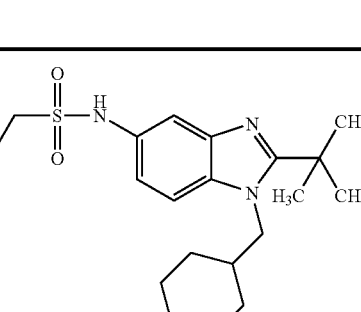 | 3.78945E−06 | 10.69 | 8.04 |
| 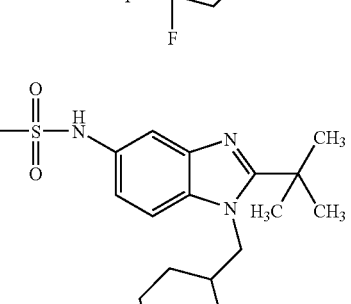 | 7.35806E−06 | 5.76 | 11.74 |

TABLE 1-continued

Metabolic stabilities (hClint and rClint) and soluabilities:

| Structure | Solubility (M) | hCLint (ul/min/mg) | rCLint (ul/min/mg) |
|---|---|---|---|
| *N-(2-tert-butyl-1-((4,4-difluorocyclohexyl)methyl)-1H-benzimidazol-5-yl)methanesulfonamide* | 4.3035E−06 | 7.41 | 23.38 |
| *N-(2-tert-butyl-1-((4,4-difluorocyclohexyl)methyl)-1H-benzimidazol-5-yl)cyclopropanesulfonamide* | 0.00000593 | 7.77 | 10.24 |
| *N-(1-((4,4-difluorocyclohexyl)methyl)-2-(1,1-difluoroethyl)-1H-benzimidazol-5-yl)cyclopropanesulfonamide* | 0.000051855 | 5.27 | <4.0 |
| *N-(2-tert-butyl-1-((4-fluorocyclohexyl)methyl)-1H-benzimidazol-5-yl)ethanesulfonamide* | 0.000353337 | 5.72 | 62.60 |

TABLE 1-continued
Metabolic stabilities (hClint and rClint) and soluabilities:
| | Solubility (M) | hCLint (ul/min/mg) | rCLint (ul/min/mg) |
|---|---|---|---|
| 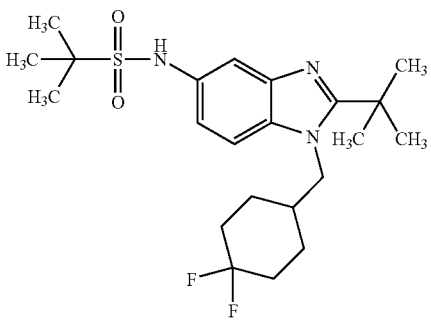 | 0.00000061 | 8.03 | 15.36 |
| 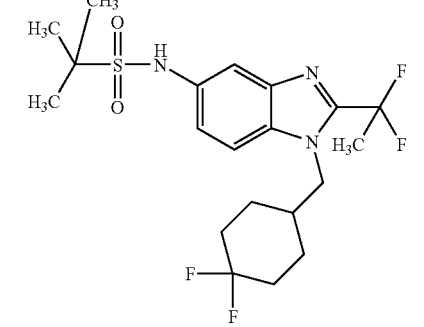 | 0.00000051 | <4.000 | 6.87 |
| 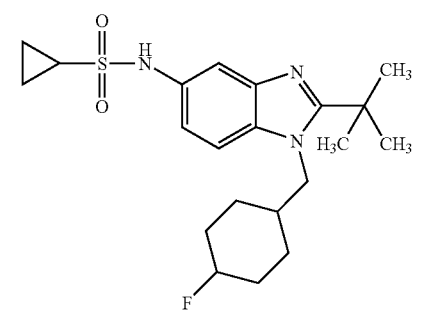 | 0.00023307 | <4.00 | N/A |
| 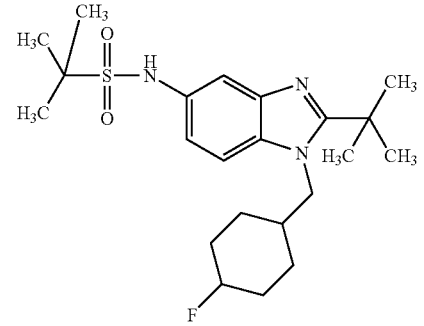 | 0.00015418 | 11.51 | N/A |

EXAMPLES

The invention will further be described in more detail by the following Examples which describe methods whereby compounds of the present invention may be prepared, purified, analyzed and biologically tested, and which are not to be construed as limiting the invention.

Example 1

N-[2-tert-Butyl-1-(tetrahydro-2H-pyran-4-ylmethyl)-1H-benzimidazol-5-yl]-N-methylcyclopropane-sulfonamide

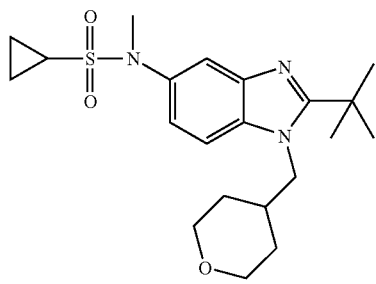

Step A: N-[2-tert-Butyl-1-(tetrahydro-2H-pyran-4-ylmethyl)-1H-benzimidazol-5-yl]-N-methylcyclo-propanesulfonamide

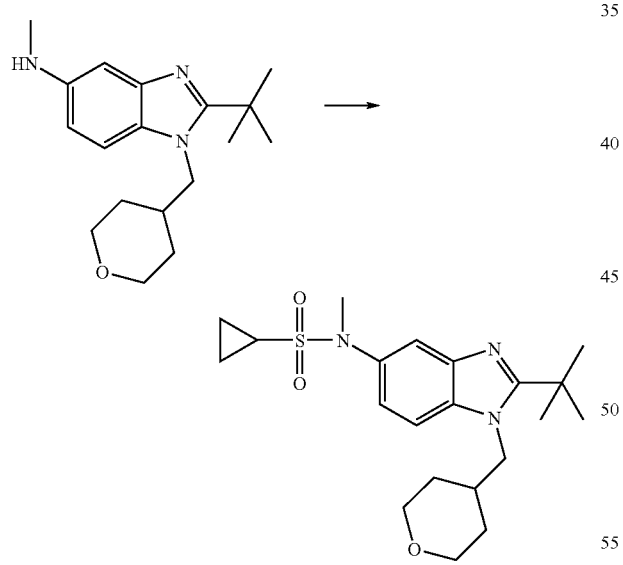

2-tert-Butyl-N-methyl-1-(tetrahydro-2H-pyran-4-ylmethyl)-1H-benzimidazol-5-amine (for preparation, see following steps B to F) (50 mg, 0.166 mmol) and a catalytic amount of DMAP were dissolved in 5 mL of DCM. Cyclopropanesulfonyl chloride (30 mg, 0.216 mmol) was added dropwise and the solution was stirred at rt overnight. The solution was washed with saturated aqueous NaHCO$_3$ solution, brine and dried over anhydrous MgSO$_4$. The product was purified by reversed-phase HPLC using 10-70% CH$_3$CN/H$_2$O and lyophilized affording the title compound as the corresponding TFA salt. Yield: 56 mg (65%). $^1$H NMR (400 MHz, MFTHANOL-D$_4$) δ 090-094 (m, 2H), 0.97-1.02 (m, 2H), 1.53-1.59 (m, 2H), 1.59-1.65 (m, 2 H), 1.69 (s, 9H), 2.36-2.42 (m, 1H), 2.60-2.65 (m, 1 H), 3.36 (m, 2 H), 3.43 (s, 3 H), 3.94 (d, J=3.58 Hz, 1 H), 3.96 (d, J=3.07 Hz, 1 H), 4.55 (d, J=7.68 Hz, 2 H), 7.74 (dd, J=8.96, 2.05 Hz, 1 H), 7.81 (d, J=1.54 Hz, 1 H), 7.98 (d, J=8.96 Hz, 1 H); MS (ESI) (M+H)$^+$ 406.0.

Step B: Methyl (4-fluoro-3-nitrophenyl)carbamate

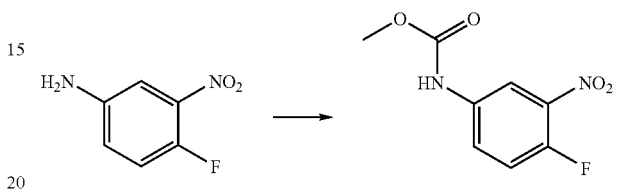

Methyl chloroformate (13.2 mL, 170.2 mmol) was added dropwise to a cold (0° C.) dichloromethane (200 mL) solution of 4-fluoro-3-nitro aniline (24.15 g, 154.7 mmol) and DIPEA (35 mL, 201 mmol). The reaction mixture was stirred at rt overnight. The solution was then diluted with 200 mL of dichloromethane and washed with 2M HCl, brine and dried over anhydrous MgSO$_4$. The solvent was concentrated and the product was directly used for the next step without further purification. Yield: 35.5 g (99%). $^1$H NMR (400 MHz, CHLOROFORM-D) δ 3.81 (s, 3H), 7.02 (s, 1H), 7.23 (m, 1H), 7.72 (d, J=8.59 Hz, 1H), 8.17 (dd, J=6.35, 2.64 Hz, 1H).

Step C: Methyl {3-nitro-4-[(tetrahydro-2H-pyran-4-ylmethyl)amino]phenyl}carbamate

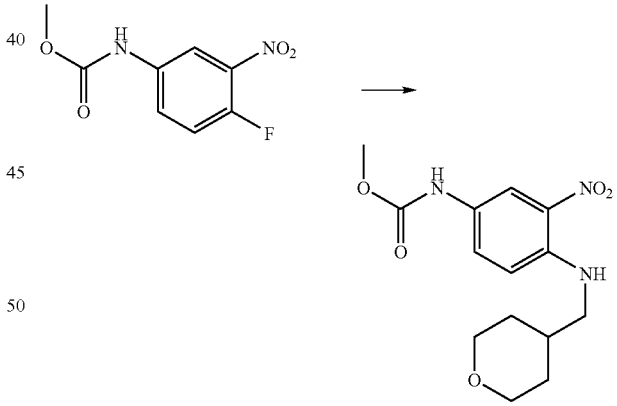

Methyl (4-fluoro-3-nitrophenyl)carbamate (2.0 g, 9.32 mmol) and 4-aminomethyl tetrahydropyran (1.28 g, 11.2 mmol) were stirred in 50 mL of EtOH containing TEA (2.0 mL, 14.0 mmol) at 75° C. for 48 h. The solvent was evaporated. The residue was dissolved in EtOAc and washed with aqueous 5% KHSO$_4$, saturated aqueous NaHCO$_3$ solution, brine and dried over anhydrous MgSO$_4$. The crude product was purified by silica gel flash chromatography using 1:1/hexanes:EtOAc as eluent. Yield: 2.53 g (88%). $^1$H NMR (400 MHz, CHLOROFORM-D) δ 1.42 (m, 2 H), 1.73 (d, J=1.76 Hz, 1 H), 1.76 (d, J=1.95 Hz, 1 H), 1.88-2.01 (m, 1 H), 3.22 (dd, J=6.74, 5.57 Hz, 2 H), 3.42 (m, 2 H), 3.78 (s, 3 H), 4.01

(d, J=4.30 Hz, 1 H), 4.04 (d, J=3.51 Hz, 1 H), 6.48 (br.s, 1 H), 6.85 (d, J=9.37 Hz, 1 H), 7.65 (br.s, 1 H), 8.03-8.09 (m, 2 H).

Step D: Methyl {3-amino-4-[(tetrahydro-2H-pyran-4-ylmethyl)amino]phenyl}carbamate

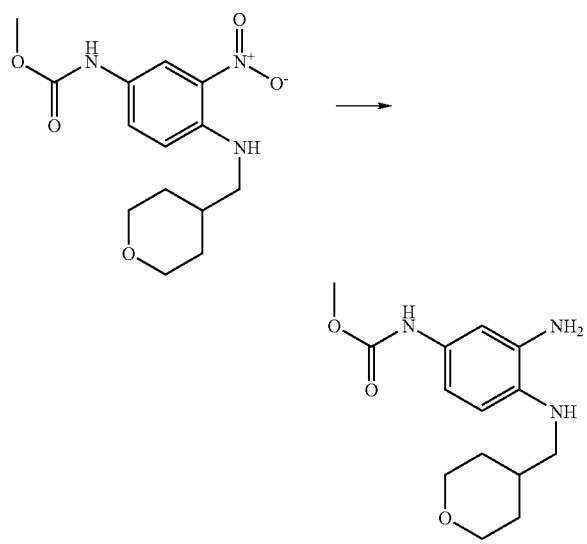

Methyl {3-nitro-4-[(tetrahydro-2H-pyran-4-ylmethyl)amino]phenyl}carbamate (2.53 g, 8.18 mmol) was dissolved in 50 mL of EtOAc containing a catalytic amount of 10% Pd/C. The solution was shaken under $H_2$ atmosphere (40 psi) using a Parr hydrogenation apparatus overnight at rt. The solution was filtered through Celite and the solvent was evaporated. Yield: 2.29 g (99%). $^1$H NMR (400 MHz, CHLOROFORM-D) δ 1.40 (m, 2 H), 1.70-1.74 (m, 1 H), 1.74-1.77 (m, 1 H), 1.81-1.92 (m, 1 H), 2.99 (d, J=6.64 Hz, 2 H), 3.34 (br.s, 2 H), 3.41 (m, 2 H), 3.74 (s, 3 H), 3.99 (d, J=3.51 Hz, 1 H), 4.02 (d, J=3.51 Hz, 1 H), 6.38 (br.s, 1 H), 6.55-6.60 (m, 1 H), 6.62-6.68 (m, 1 H), 6.95 (br.s, 1 H).

Step E: Methyl [2-tert-butyl-1-(tetrahydro-2H-pyran-4-ylmethyl)-1H-benzimidazol-5-yl]carbamate

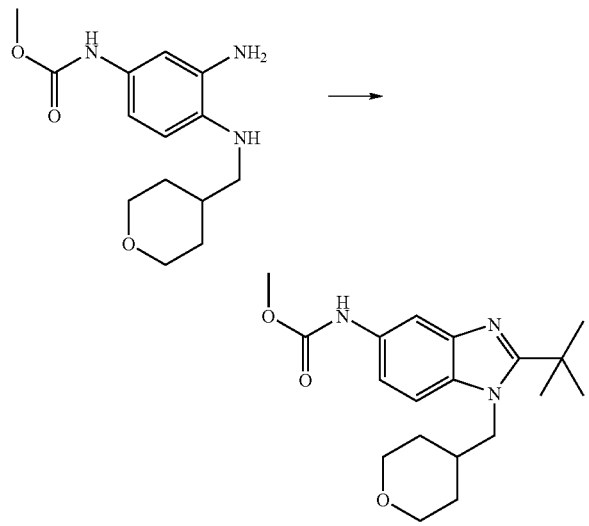

Methyl {3-amino-4-[(tetrahydro-2H-pyran-4-ylmethyl)amino]phenyl}carbamate (2.29 g, 8.20 mmol) and DMAP (0.20 g, 1.64 mmol) were dissolved in 75 mL of DCM. Trimethylacetyl chloride (1.10 mL, 9.02 mmol) was added dropwise and the solution was stirred at rt for 2 h. The solution was washed with aqueous $NaHCO_3$ solution, brine and dried over anhydrous $MgSO_4$. The residue was dissolved in 25 mL of AcOH and was heated at 125° C. for 1 h using a Personal Chemistry microwave apparatus. The solvent was evaporated. The residue was dissolved in EtOAc and washed with aqueous $NaHCO_3$ solution, brine and dried over anhydrous $MgSO_4$. The crude product was purified by silica gel flash chromatography using 4:3/hexanes: acetone as eluent. Yield: 1.81 g (64%). $^1$H NMR (400 MHz, CHLOROFORM-D) δ 1.48-1.54 (m, 4 H), 1.56 (s, 9 H), 2.23-2.35 (m, 1 H), 3.27-3.35 (m, 2 H), 3.78 (s, 3 H), 3.96 (t, J=2.93 Hz, 1 H), 3.99 (t, J=3.03 Hz, 1 H), 4.18 (d, J=7.42 Hz, 2 H), 6.63 (br.s, 1 H), 7.24-7.28 (m, 1 H), 7.41 (br.s, 1 H), 7.61 (d, J=1.95 Hz, 1 H).

Step F: 2-tert-Butyl-N-methyl-1-(tetrahydro-2H-pyran-4-ylmethyl)-1H-benzimidazol-5-amine

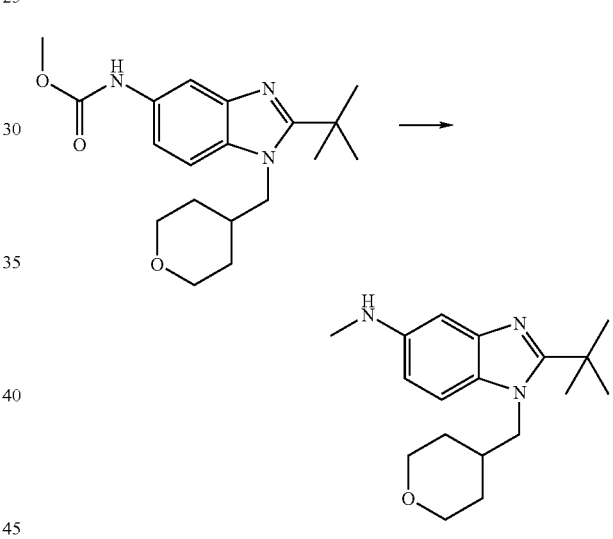

Methyl [2-tert-butyl-1-(tetrahydro-2H-pyran-4-ylmethyl)-1H-benzimidazol-5-yl]carbamate (1.80 g, 5.21 mmol) was dissolved in 75 mL of THF at 0° C. 1M HCl/ether (7.3 mL, 7.29 mmol) was added dropwise and the solution was stirred at 0° C. for 15 min. $LiAlH_4$ (988 mg, 26.1 mmol) was added slowly and the solution was stirred at rt overnight. The reaction was quenched at 0° C. by the addition of MeOH (5 mL) followed by water (10 mL) and the solution was left to stir at rt for 30 min. Anhydrous $Na_2SO_4$ (10 g) was added and the solution was stirred at rt for another 30 min. The solution was filtered and the solvent was evaporated. The residue was dissolved in EtOAc and washed with aqueous $NaHCO_3$ solution, brine and dried over anhydrous $MgSO_4$. The solvent was evaporated. Yield: 1.54 g (98%). $^1$H NMR (400 MHz, CHLOROFORM-D) δ 1.49-1.53 (m, 4 H), 1.53-1.57 (m, 9 H), 2.22-2.32 (m, 1 H), 2.87 (s, 3 H), 3.26-3.35 (m, 2 H), 3.95 (t, J=3.03 Hz, 1 H), 3.97-4.00 (m, 1 H), 4.13 (d, J=7.42 Hz, 2 H), 6.61 (dd, J=8.59, 2.15 Hz, 1 H), 6.99 (d, J=1.95 Hz, 1 H), 7.11 (d, J=8.59 Hz, 1 H).

Example 2

N-[2-tert-Butyl-1-(tetrahydro-2H-pyran-4-ylmethyl)-1H-benzimidazol-5-yl]-N-methylpropane-1-sulfonamide

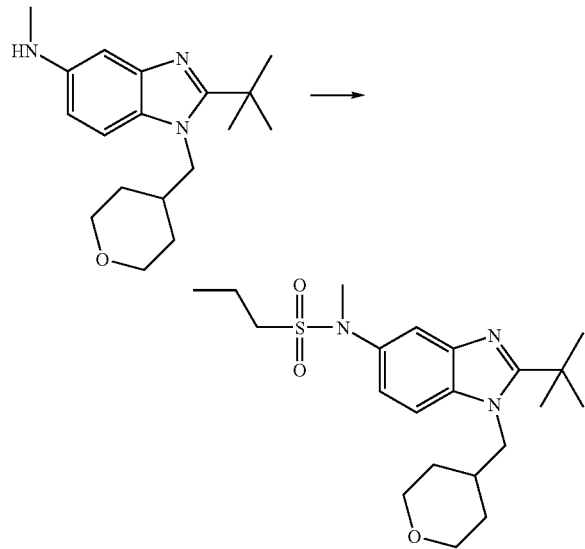

2-tert-Butyl-N-methyl-1-(tetrahydro-2H-pyran-4-ylmethyl)-1H-benzimidazol-5-amine (for preparation, see Steps B to F of Example 1) (50 mg, 0.166 mmol) and a catalytic amount of DMAP were dissolved in 5 mL of DCM. 1-Propanesulfonyl chloride (0.024 mL, 0.216 mmol) was added dropwise and the solution was stirred at rt for 3 h. The solution was washed with saturated aqueous NaHCO$_3$ solution, brine and dried over anhydrous MgSO$_4$. The product was purified by reversed-phase HPLC using 10-70% CH$_3$CN/H$_2$O and lyophilized affording the title compound as the corresponding TFA salt. Yield: 60 mg (69%); $^1$H NMR (400 MHz, METHANOL-D$_4$) δ 1.02 (t, J=7.42 Hz, 3 H), 1.54-1.59 (m, 2 H), 1.60-1.66 (m, 2 H), 1.69 (s, 9 H), 1.76-1.83 (m, 2 H), 2.36-2.42 (m, 1 H), 3.09-3.13 (m, 2 H), 3.36 (m, 2 H), 3.40 (s, 3 H), 3.94 (d, J=3.58 Hz, 1 H), 3.95 (d, J=3.58 Hz, 1 H), 4.55 (d, J=7.68 Hz, 2 H), 7.70 (dd, J=8.96, 2.05 Hz, 1 H), 7.81 (d, J=1.79 Hz, 1 H), 7.98 (d, J=8.96 Hz, 1 H); MS (ESI) (M+H)$^-$ 408.0.

Example 3

N-[2-tert-Butyl-1-(tetrahydro-2H-pyran-4-ylmethyl)-1H-benzimidazol-5-yl]-N-methylbutane-1-sulfonamide

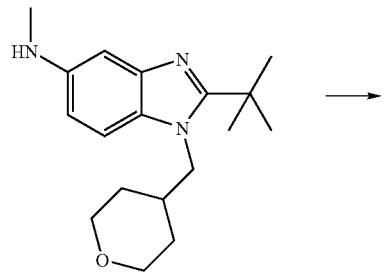

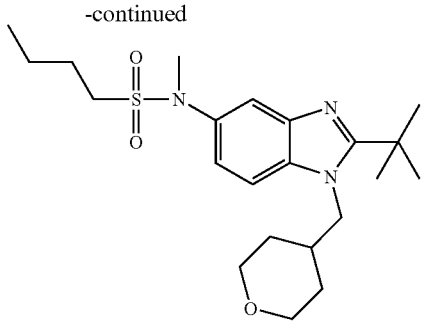

2-tert-Butyl-N-methyl-1-(tetrahydro-2H-pyran-4-ylmethyl)-1H-benzimidazol-5-amine (for preparation see Steps B, C, D, E and F of Example 1) (38 mg, 0.126 mmol) and 1-butanesulfonyl chloride (0.025 mL, 0.189 mmol) were stirred in 3 mL of DCM containing a catalytic amount of DMAP at rt overnight. The solvent was evaporated and the product was purified by reversed-phase HPLC using 10-60% CH$_3$CN/H$_2$O and lyophilized affording the title compound as the corresponding TFA salt. Yield: 39 mg (58%). $^1$H NMR (400 MHz, METHANOL-D$_4$): δ 0.88-0.94 (m, 3 H), 1.43 (m, 2 H), 1.53-1.59 (m, 2 H) 1.59-1.66 (m, 2 H), 1.69 (s, 9 H), 1.71-1.77 (m, 2 H), 2.35-2.42 (m, 1 H), 3.10-3.16 (m, 2 H), 3.35 (m, 2 H), 3.40 (s, 3 H), 3.93 (d, J=3.12 Hz, 1 H), 3.96 (d, J=3.71 Hz, 1 H), 4.54 (d, J=7.42 Hz, 2 H), 7.69 (dd, J=8.98, 2.15 Hz, 1 H), 7.81 (d, J=1.56 Hz, 1 H), 7.97 (d, J=8.98 Hz, 1 H); MS (ESI) (M+H)$^+$ 422.2; Anal. Calcd for C$_{22}$H$_{35}$N$_3$O$_3$S+1.3 TFA+1.2 H$_2$O: C, 49.96; H, 6.60; N, 7.10. Found: C, 49.98; H, 6.67; N, 6.83.

Example 4

N-{2-tert-Butyl-1-[(4,4-difluorocyclohexyl)methyl]-1H-benzimidazol-5-yl}-N-methylbutane-1-sulfonamide

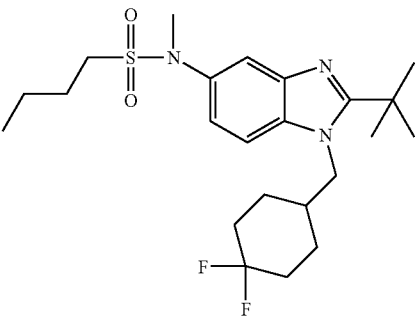

Step A: N-{2-tert-Butyl-1-[(4,4-difluorocyclohexyl)methyl]-1H-benzimidazol-5-yl}-N-methylbutane-1-sulfonamide

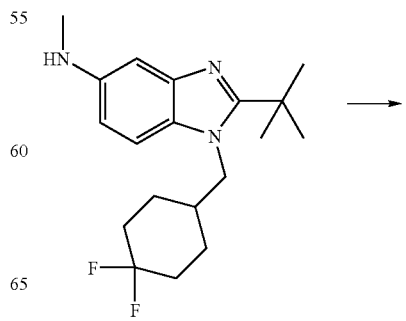

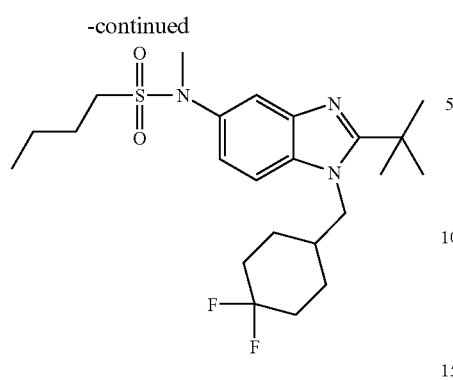

2-tert-Butyl-1-[(4,4-difluorocyclohexyl)methyl]-N-methyl-1H-benzimidazol-5-amine (for preparation see following Steps B. C, D, E, F and G) (46 mg, 0.137 mmol) and 1-butanesulfonyl chloride (0.063 mL, 0.411 mmol) were stirred in 3 mL of DCM containing a catalytic amount of DMAP at rt for 6 h. The solvent was evaporated and the product was purified by reversed-phase HPLC using 10-75% $CH_3CN/H_2O$ and lyophilized affording the title compound as the corresponding TFA salt. Yield: 48 mg (62%). $^1H$ NMR (400 MHz, MFTHANOL-$D_4$): δ 0.92 (t, J=7.32 Hz, 3 H), 1.43 (m, 2 H), 1.52-1.63 (m, 2 H), 1.69 (s, 9 H), 1.70-1.76 (m, 4 H), 1.76-1.84 (m, 2 H), 2.02-2.12 (m, 2H), 2.22-2.31 (m, 1 H), 3.10-3.17 (m, 2H), 3.41 (s, 3 H), 4.56 (d, J=7.62 Hz, 2 H), 7.69 (dd, J=8.98, 2.15 Hz, 1 H), 7.82 (d, J=1.76 Hz, 1 H), 7.96 (d, J=9.18 Hz, 1 H); MS (ESI) (M+H)$^+$ 456.

Step B: tert-Butyl [(4,4-difluorocyclohexyl)methyl]carbamate

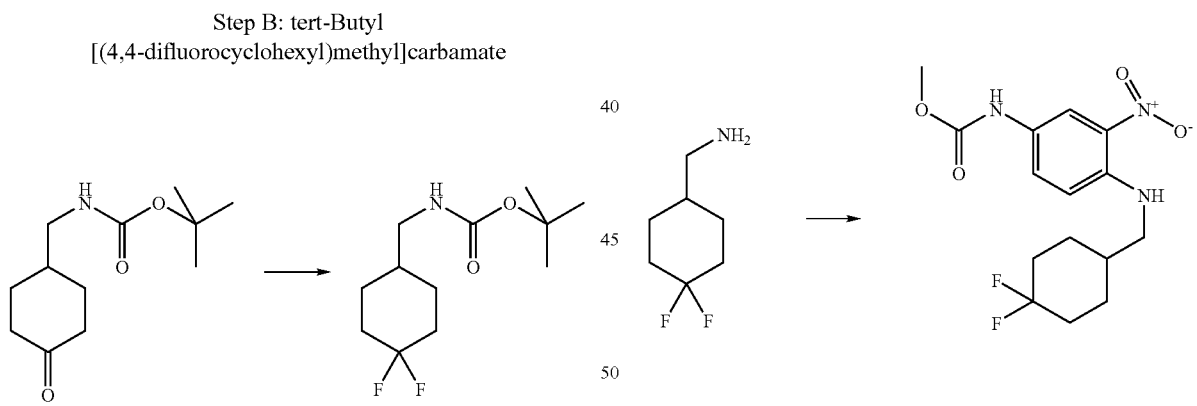

4-N-Boc-aminomethyl cyclohexanone (1.00 g, 4.4 mmol) was dissolved in 30 mL of DCM at 0° C. DAST (1.45 mL, 11.0 mmol) was added dropwise and the solution was stirred at rt overnight. The solution was washed with aqueous 5% $KHSO_4$ solution, saturated aqueous $NaHCO_3$ solution, brine and dried over anhydrous $MgSO_4$. The crude product was purified by silica gel flash chromatography using 3:1/hexanes EtOAc as eluent. Yield: 508 mg (46%). $^1H$ NMR (400 MHz, CHLOROFORM-D): δ 1.19-1.36 (m, 2 H), 1.44 (s, 9 H), 1.51-1.56 (m, 1 H), 1.59-1.75 (m, 2 H), 1.75-1.84 (m, 2 H), 2.01-2.16 (m, 2 H), 3.03 (t, J=6.54 Hz, 2 H), 4.62 (br.s, 1 H).

Step C: [(4,4-Difluorocyclohexyl)methyl]amine hydrochloride

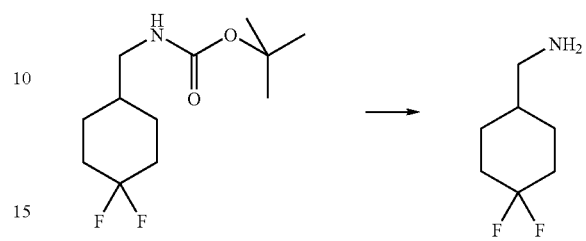

tert-Butyl [(4,4-difluorocyclohexyl)methyl]carbamate (505 mg, 2.03 mmol) was stirred in 5 mL of 1M HCl/AcOH at rt for 2 h. The solvent was evaporated. The residue was washed with ether, filtered and dried. Yield: 330 mg (88%). $^1H$ NMR (400 MHz, METHANOL-$D_4$): δ 1.28-1.40 (m, 2 H), 1.71-1.82 (m, 2 H), 1.84 (d, J=3.12 Hz, 2 H), 1.86-1.89 (m, 1 H), 2.03-2.15 (m, 2 H), 2.85 (d, J=7.03 Hz, 2 H).

Step D: Methyl (4-{[(4,4-difluorocyclohexyl)methyl]amino}-3-nitrophenyl)carbamate Following the same procedure as in Step C of Example 1 using [(4,4-difluorocyclohexyl)methyl]amine hydrochloride (210 mg, 1.12 mmol), methyl (4-fluoro-3-nitrophenyl)carbamate (200 mg, 0.934 mmol) and TEA (0.390 mL, 2.80 mmol) in 10 mL of EtOH. The crude product was purified by silica gel flash chromatography using 5% ether/DCM as eluent. Yield: 200 mg (62%). $^1H$ NMR (400 MHz, CHLOROFORM-D): δ 1.34-1.47 (m, 2 H), 1.65-1.75 (m, 2 H), 1.78-1.85 (m, 1 H), 1.90-1.93 (m, 1 H), 1.94-1.97 (m, 1 H), 2.10-2.21 (m, 2 H), 3.23 (dd, J=6.64, 5.66 Hz, 2 H), 3.78 (s, 3 H), 6.48 (br.s, 1 H), 6.83 (d, J=9.18 Hz, 1 H), 7.66 (br.s, 1 H), 8.05 (br.s, 1 H), 8.07 (d, J=2.54 Hz, 1 H).

Step E: Methyl (3-amino-4-{[(4,4-difluorocyclohexyl)methyl]amino}phenyl)carbamate

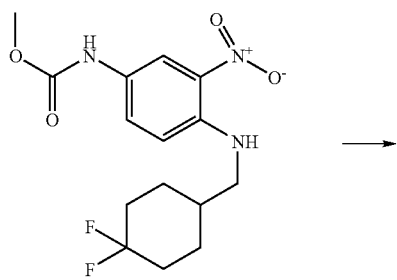

Following the same procedure as in Step D of Example 1 using methyl (4-{[(4,4-difluorocyclohexyl)methyl]amino}-3-nitrophenyl)carbamate (200 mg, 0.583 mmol) and a catalytic amount of 10% Pd/C in 20 mL of EtOAc. Yield: 185 mg (99%). MS (ESI) (M+H)+314.29.

Step F: Methyl {2-tert-butyl-1-[(4,4-difluorocyclohexyl)methyl]-1H-benzimidazol-5-yl}carbamate

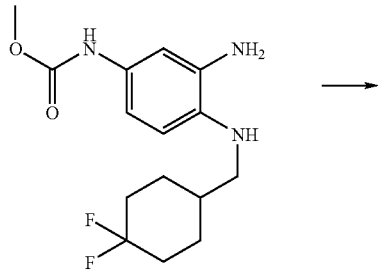

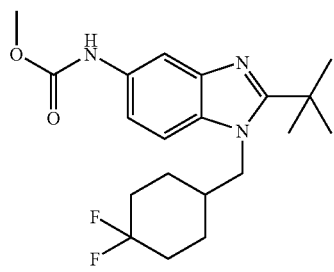

Methyl (3-amino-4-{[(4,4-difluorocyclohexyl)methyl]amino}phenyl)carbamate (185 mg, 0.590 mmol) and DMAP (15 mg, 0.118 mmol) were dissolved in 10 mL of DCM. Trimethylacetyl chloride (0.080 mL, 0.649 mmol) was added dropwise and the solution was stirred at rt for 2 h. The solution was washed with aqueous NaHCO₃ solution, brine and dried over anhydrous MgSO₄. The solvent was concentrated. The residue was dissolved in 4 mL of DCE and P₂O₅ (catalytic) was added and the solution was heated at 125° C. for 1 h using a Personal Chemistry microwave apparatus.

The solution was washed with aqueous NaHCO₃ solution, brine and dried over anhydrous MgSO₄. The crude product was purified by silica gel flash chromatography using 50 to 75% EtOAc/hexanes. Yield: 122 mg (54%); $^1$H NMR (400 MHz, CHLOROFORM-D): δ 1.43-1.52 (m, 2 H), 1.55 (s, 9 H), 1.57-1.66 (m, 2 H), 1.67-1.74 (m, 2 H), 2.08-2.18 (m, 3 H), 3.79 (s, 3 H), 4.19 (d, J=7.42 Hz, 2 H), 6.63 (br.s, 1 H), 7.23 (d, J=8.79 Hz, 1 H), 7.37-7.46 (m, 1 H), 7.62 (d, J=1.76 Hz, 1 H).

Step G: 2-tert-Butyl-1-[(4,4-difluorocyclohexyl)methyl]-N-methyl-1H-benzimidazol-5-amine

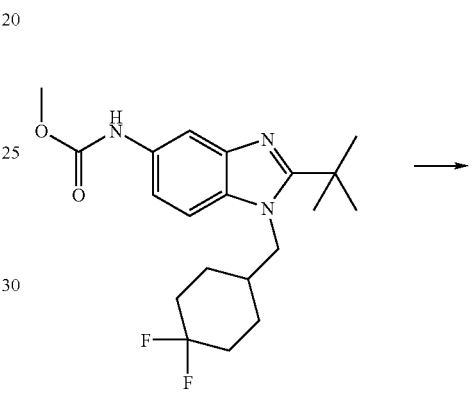

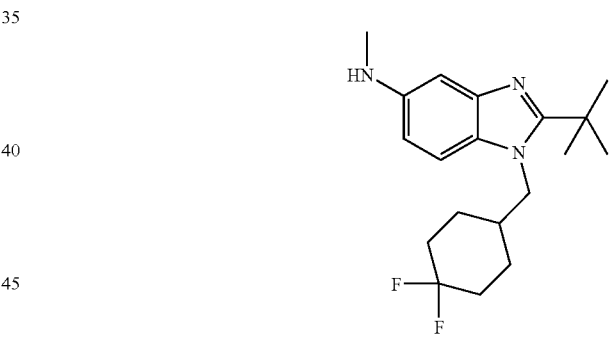

Methyl {2-tert-butyl-1-[(4,4-difluorocyclohexyl)methyl]-1H-benzimidazol-5-yl}carbamate (115 mg, 0.303 mmol) was dissolved in 10 mL of THF at 0° C. 1M HCl/ether (0.425 mL, 0.424 mmol) was added and the solution was stirred at 0° C. for 15 min. LiAlH₄ (57 mg, 1.52 mmol) was added slowly and the solution was stirred at rt overnight. The reaction was quenched at 0° C. by the addition of MeOH (1 mL) and water (2 mL). Anhydrous Na₂SO₄ (5.0 g) was added and the solution was stirred at rt for 30 min. The solution was filtered and the solvent was evaporated. The residue was dissolved in EtOAc and washed with saturated aqueous NaHCO₃ solution, brine and dried over anhydrous MgSO₄. Yield: 95 mg (93%). $^1$H NMR (400 MHz, CHLOROFORM-D): δ 1.41-1.51 (m, 2 H), 1.54 (s, 9 H), 1.57-1.67 (m, 2 H), 1.68-1.76 (m, 3 H), 2.07-2.17 (m, 3 H), 2.87 (s, 3 H), 4.15 (d, J=7.42 Hz, 2 H), 6.61 (dd, J=8.59, 2.34 Hz, 1 H), 7.01 (d, J=1.95 Hz, 1 H), 7.09 (d, J=8.59 Hz, 1 H).

Example 5

N-Methyl-N-[1-(tetrahydro-2H-pyran-4-ylmethyl)-2-(trifluoromethyl)-1H-benzimidazol-5-yl]propane-1-sulfonamide

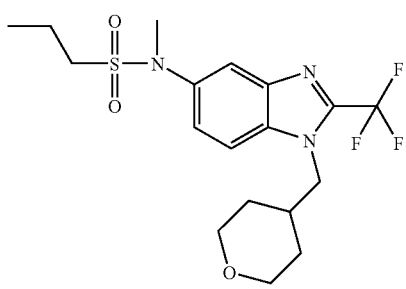

Step A: N-Methyl-N-[1-(tetrahydro-2H-pyran-4-ylmethyl)-2-(trifluoromethyl)-1H-benzimidazol-5-yl]propane-1-sulfonamide

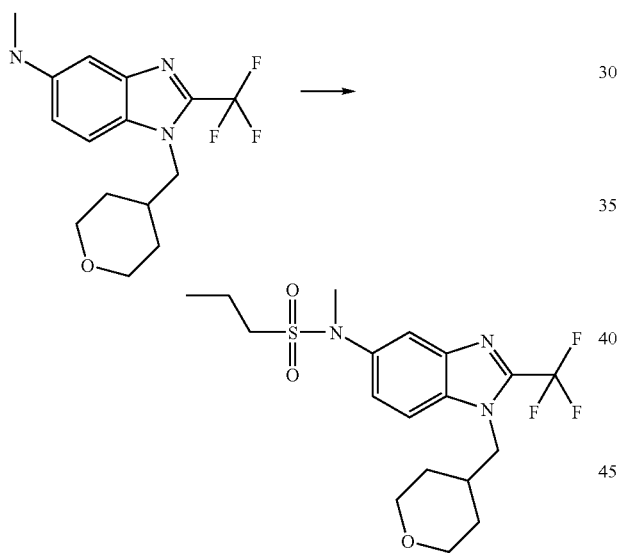

Propane-1-sulfonyl chloride (27 uL, 34 mg, 0.24 mmol) was added to a solution of N-methyl-1-(tetrahydro-2H-pyran-4-ylmethyl)-2-(trifluoromethyl)-1H-benzimidazol-5-amine (63 mg, 0.20 mmol) (see following steps B, C, D, E, F and G for preparation), DIPEA (49 uL, 36 mg, 0.28 mmol) and DMAP (5 mg, 0.04 mmol) in DCM (6 mL) at 0° C. The reaction mixture was stirred overnight at room temperature, diluted with DCM (50 mL), washed with saturated NaHCO$_3$ (2×10 mL) and dried over Na$_2$SO$_4$. The crude product was purified by MPLC using Hex/EtOAc (1:1) on silica gel to give 40 mg (47%) of a white solid as the title compound. $^1$HNMR (400 MHz, METHANOL-D$_4$): δ 1.00 (t, J=7.42 Hz, 3 H), 1.38-1.53 (m, 4 H), 1.70-1.88 (m, 2 H), 2.15-2.30 (m, 1 H), 3.01-3.11 (m, 2 H), 3.28-3.33 (m, 2 H), 3.35 (s, 3 H), 3.88-3.91 (m, 2 H), 4.30 (d, J=7.62 Hz, 2 H), 7.55 (dd, J=8.79, 1.76 Hz, 1 H), 7.75 (d, J=8.98 Hz, 1 H), 7.82 (d, J=1.56 Hz, 1 H). MS (ESI) (M+H)$^+$=420.0. Anal. Calcd for C$_{18}$H$_{24}$F$_3$N$_3$O$_3$S+ 0.20 H$_2$O+0.30 CH$_3$OH (432.68): C, 50.80; H, 5.96; N, 9.71. Found: C, 50.79; H, 5.91; N, 9.69.

Step B. N-(4-fluoro-3-nitrophenyl)acetamide

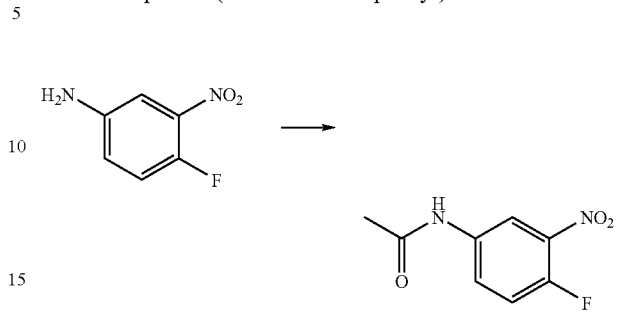

4-Fluoro-3-nitro-aniline (45.0 g, 0.288 mol) was added in portions to acetic anhydride (150 mL) at room temperature. The reaction mixture was stirred at room temperature for 2 h. The white solid was collected and dried in vacuo to give the title compound (42.0 g, 70%). $^1$H NMR (400 MHz, CHLOROFORM-D): δ 2.23 (s, 3 H), 7.26 (m, 1 H), 7.50 (s broad, 1 H), 7.87 (m, 1 H), 8.23 (dd, J=6.44, 2.73 Hz, 1 H).

Step C: N-(4-fluoro-3-nitrophenyl)-N-methylacetamide

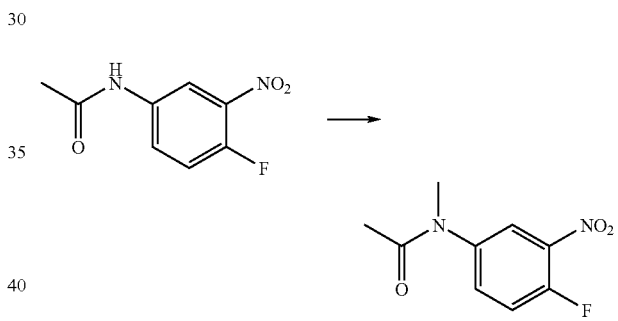

Sodium hydride (4.22 g, 60%, 106 mmol) was added portionwise to a solution of N-(4-fluoro-3-nitrophenyl)acetamide (13.9 g, 70 mmol) in THF (200 mL) at 0° C. Stirring for 20 min, iodomethane (18.5 g, 130 mmol) was added. The reaction mixture was stirred at room temperature for 2 h, quenched with saturated NaHCO$_3$ (30 mL) and extracted with EtOAc (3×100 mL). The combined organic phases were washed with saturated NaCl (2×50 mL). After filtration and concentration, 13.1 g (88%) of the title compound was obtained as a yellow solid. $^1$H NMR (400 MHz, CHLOROFORM-D): δ 1.92 (s, 3 H), 3.30 (s, 3 H), 7.38 (s, 1 H), 7.52 (s, 1 H), 7.95 (s, 1 H).

Step D. N-methyl-N-{3-nitro-4-[(tetrahydro-2H-pyran-4-ylmethyl)amino]phenyl}acetamide

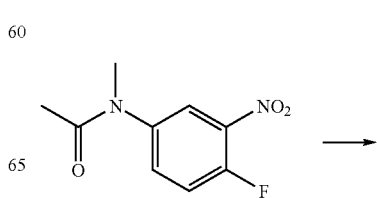

-continued

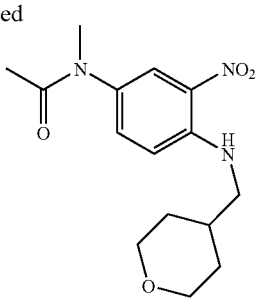

4-Aminomethyltetrahydropyran (10.0 g, 86.5 mmol) was added to a mixture of N-(4-fluoro-3-nitrophenyl)-N-methylacetamide (15.6 g, 73.3 mmol) and TEA (15.3 mL, 11.1 g, 110 mmol) in EtOH (300 mL) at room temperature. The reaction mixture was heated for 6 h at reflux. Upon evaporation of ethanol, the residue was dissolved in EtOAc (400 mL), washed with $H_2O$ (3×50 mL), saturated NaCl (3×50 mL), and dried over $Na_2SO_4$. After filtration and concentration, 21.7 g (96%) of the title compound was obtained as an orange-red solid. $^1H$ NMR (400 MHz, CHLOROFORM-D): δ 1.38-1.52 (m, 2 H), 1.72-1.81 (m, 2 H), 1.90 (s, 3 H), 1.93-2.02 (m, 1 H), 3.23 (s, 3 H), 3.23-3.27 (m, 2 H), 3.36-3.49 (m, 2 H), 4.01-4.07 (m, 2 H), 6.91 (d, J=9.18 Hz, 1 H), 7.29 (dd, J=9.08, 2.64 Hz, 1 H), 8.05 (d, J=2.34 Hz, 1 H), 8.22 (t, J=5.37 Hz, 1 H). MS (ESI) $(M+H)^+$=309.12.

Step E. N-{3-Amino-4-[(tetrahydro-2H-pyran-4-ylmethyl)amino]phenyl}-N-methylacetamide

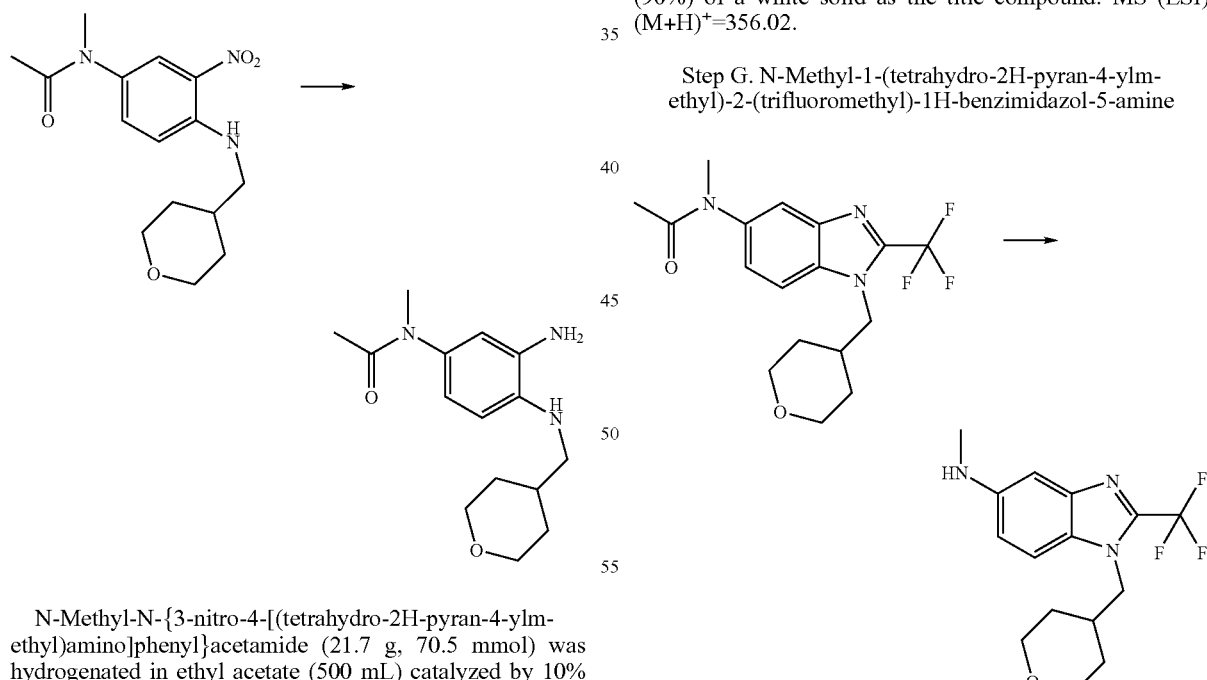

N-Methyl-N-{3-nitro-4-[(tetrahydro-2H-pyran-4-ylmethyl)amino]phenyl}acetamide (21.7 g, 70.5 mmol) was hydrogenated in ethyl acetate (500 mL) catalyzed by 10% Pd/C (1.0 g) at 30-40 psi $H_2$ in Parr shaker for 18 h at room temperature. After filtration through celite and concentration, 19.6 g (100%) of a purple solid was obtained. $^1H$ NMR (400 MHz, CHLOROFORM-D): δ 1.35-1.50 (m, 2 H), 1.67 (s, 1 H), 1.73-1.81 (m, 2 H), 1.88 (s, 3 H), 1.88-1.99 (m, 1 H), 3.04 (d, J=6.64 Hz, 2 H), 3.20 (s, 3 H), 3.33-3.48 (m, 4 H), 3.97-4.08 (m, 2 H), 6.54 (d, J=1.76 Hz, 1 H), 6.60-6.63 (m, 2 H); MS (ESI) $(M+H)^+$: 278.7

Step F. N-Methyl-N-[1-(tetrahydro-2H-pyran-4-ylmethyl)-2-(trifluoromethyl)-1H-benzimidazol-5-yl]acetamide

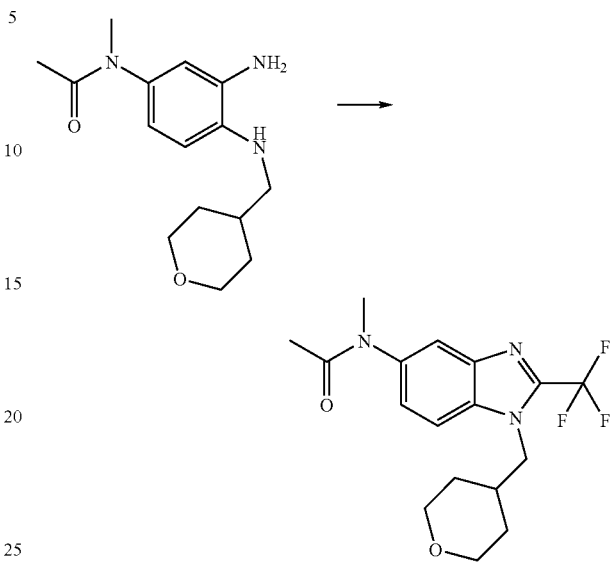

A solution of N-{3-amino-4-[(tetrahydro-2H-pyran-4-ylmethyl)amino]phenyl}-N-methylacetamide hydrochloride (2.77 g, 10 mmol) in trifluoroacetic acid (60 mL) was heated to reflux for 18 h. After evaporation of the solvent, the residue was dissolved in EtOAc (200 mL), washed with 2N NaOH (2×10 mL) and dried over $Na_2SO_4$. The crude product was purified by MPLC using EtOAc on silica gel to give 3.18 g (90%) of a white solid as the title compound. MS (ESI) $(M+H)^+$=356.02.

Step G. N-Methyl-1-(tetrahydro-2H-pyran-4-ylmethyl)-2-(trifluoromethyl)-1H-benzimidazol-5-amine N-Methyl-N-[1-(tetrahydro-2H-pyran-4-ylmethyl)-2-(trifluoromethyl)-1H-benzimidazol-5-yl]acetamide (3.18 g, 8.95 mmol) was dissolved in hydrochloric acid (37%, 60 mL) and then heated overnight at 95° C. After concentration, the residue was treated with 20 mL of 2N NaOH, extracted with EtOAc (4×50 mL). The combined organic phases were washed with brine (20 mL) and dried over $Na_2SO_4$. After evaporation, 2.80 g (100%) of a purple white solid was obtained as the title product, which was used directly for Step H. MS (ESI) (M+H)$^+$=314.20.

Example 6

N-Methyl-N-[1-(tetrahydro-2H-pyran-4-ylmethyl)-2-(trifluoromethyl)-1H-benzimidazol-5-yl]cyclopropanesulfonamide

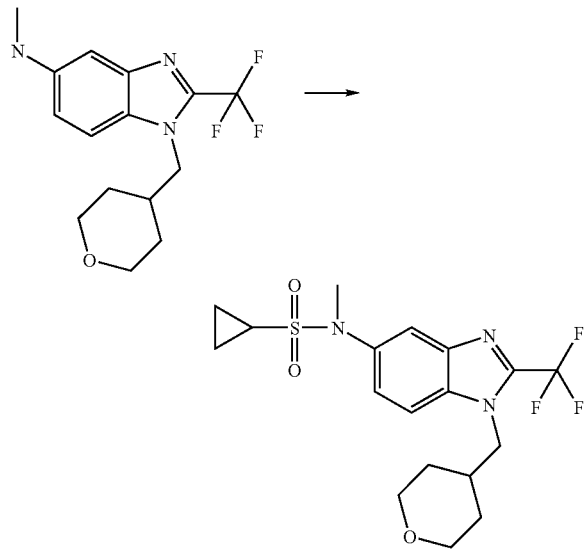

Following the procedure in Example 5, using cyclopropanesulfonyl chloride (34 mg, 0.24 mmol), N-methyl-1-(tetrahydro-2H-pyran-4-ylmethyl)-2-(trifluoromethyl)-1H-benzimidazol-5-amine (63 mg, 0.20 mmol) (for preparation, see the step G in example 1), DIPEA (49 uL, 36 mg, 0.28 mmol) and DMAP (5 mg, 0.04 mmol) in DCM (6 mL) at 0° C. The crude product was purified by MPLC using Hex/EtOAc (1:1) on silica gel to give 81 mg (97%) of a white solid as the title compound. $^1$HNMR (400 MHz, METHANOL-D$_4$): δ 0.85-0.92 (m, 2 H), 0.93-1.01 (m, 2 H), 1.37-1.52 (m, 4 H), 2.18-2.31 (m, 1 H), 2.55-2.65 (m, 1 H), 3.30-3.36 (m, 2 H), 3.38 (s, 3 H), 3.86-3.95 (m, 2 H), 4.32 (d, J=7.62 Hz, 2 H), 7.58 (dd, J=8.89, 2.05 Hz, 1 H), 7.76 (d, J=8.79 Hz, 1 H) 7.86 (d, J=1.95 Hz, 1 H). MS (ESI) (M+H)+=418.0. Anal. Calcd for C$_{18}$H$_{22}$F$_3$N$_3$O$_3$S+0.10 H$_2$O+0.20 CH$_3$OH (425.66): C, 51.36; H, 5.45; N, 9.87. Found: C, 51.39; H, 5.49; N, 9.92.

Example 7

N-[2-tert-Butyl-1-(tetrahydro-2H-pyran-4-ylmethyl)-1H-benzimidazol-5-yl]-N-methylpentane-1-sulfonamide

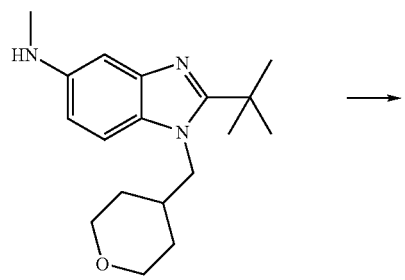

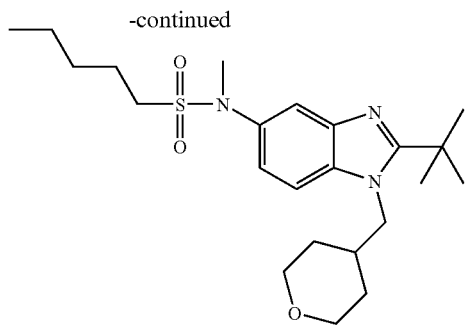

2-tert-Butyl-N-methyl-1-(tetrahydro-2H-pyran-4-ylmethyl)-1H-benzimidazol-5-amine (65 mg, 0.216 mmol) and a catalytic amount of DMAP were dissolved in 3 mL of DCE. n-Pentylsulfonyl chloride (44 mg, 0.259 mmol) was added and the solution was stirred at rt for 4 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 89 mg (75%). $^1$H NMR (400 MHz, METHANOL-D$_4$) δ 0.89 (t, J=7.13 Hz, 3 H), 1.26-1.34 (m, 2 H), 1.34-1.43 (m, 2 H), 1.52-1.58 (m, 2 H), 1.58-1.66 (m, 2 H), 1.69 (s, 9 H), 1.71-1.80 (m, 2 H), 2.34-2.43 (m, 1 H), 3.09-3.16 (m, 2 H), 3.36 (td, J=11.47, 2.64 Hz, 2 H), 3.40 (s, 3 H) 3.93 (d, J=3.12 Hz, 1 H), 3.95-3.97 (m, 1 H), 4.55 (d, J=7.62 Hz, 2 H), 7.69 (dd, J=9.08, 2.05 Hz, 1 H), 7.81 (d, J=1.56 Hz, 1 H), 7.97 (d, J=8.59 Hz, 1 H); MS (ESI) (M+H)$^+$ 436.0; Anal. Calcd (%) for C$_{23}$H$_{37}$N$_3$O$_3$S+1.1 TFA+ 0.9 H$_2$O; C, 52.43; H, 6.97; N, 7.28. Found: C, 52.39; H, 6.96; N, 7.43.

Example 8

N-[2-tert-Butyl-1-(tetrahydro-2H-pyran-4-ylmethyl)-1H-benzimidazol-5-yl]-N-methylethanesulfonamide

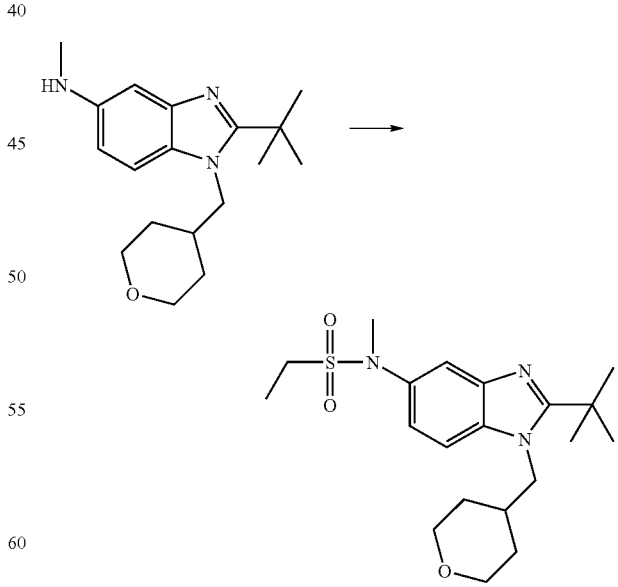

2-tert-Butyl-N-methyl-1-(tetrahydro-2H-pyran-4-ylmethyl)-1H-benzimidazol-5-amine (50 mg, 0.166 mmol) and a catalytic amount of DMAP were dissolved in 3 mL of DCE. Ethanesulfonyl chloride (0.020 mL, 0.215 mmol) was added and the solution was stirred at rt for 12 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 70 mg (83%). $^1$H NMR (600 MHz, CD$_3$OD) δ 1.31 (t, J=7.30 Hz, 3 H), 1.53-1.58 (m, 2 H), 1.58-1.65 (m, 2 H), 1.69 (s, 9 H), 2.35-2.42 (m, 1 H), 3.16 (m, 2 H), 3.35 (m, 2 H), 3.41 (s, 3 H), 3.94 (d, J=3.84 Hz, 1 H), 3.95 (d, J=3.84 Hz, 1 H), 4.54 (d, J=7.68 Hz, 2 H), 7.69 (dd, J=9.09, 1.92 Hz, 1 H), 7.81 (d, J=1.79 Hz, 1 H), 7.97 (d, J=8.96 Hz, 1 H); MS (ESI) (M+H)$^+$ 394.0; Anal. Calcd (%) for C$_{20}$H$_{31}$N$_3$O$_3$S+1.4 TFA: C, 49.50; H, 5.90; N, 7.60. Found: C, 49.51; H, 6.00; N, 7.24.

Example 9

N-[2-tert-Butyl-1-(tetrahydro-2H-pyran-4-ylmethyl)-1H-benzimidazol-5-yl]-N,2-dimethylpropane-2-sulfonamide

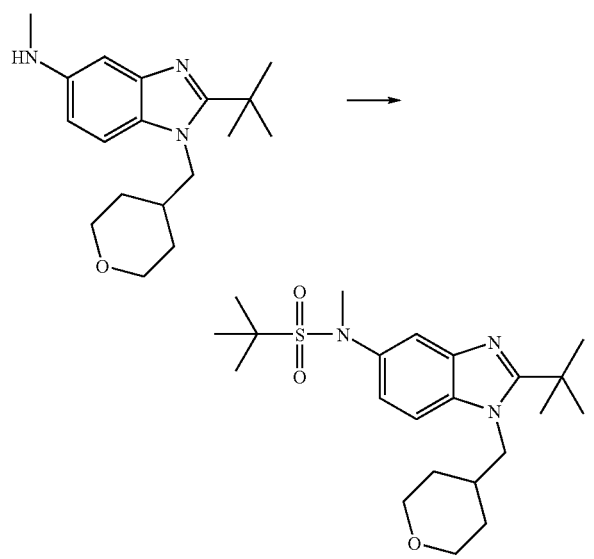

2-tert-Butyl-N-methyl-1-(tetrahydro-2H-pyran-4-ylmethyl)-1H-benzimidazol-5-amine (50 mg, 0.166 mmol) and DMAP (20 mg, 0.166 mmol) were dissolved in 3 mL of DCM. t-Butylsulfinyl chloride (0.027 mL, 0.215 mmol) was added and the solution was stirred at rt for 2 h. The solution was washed with saturated aqueous NaHCO$_3$ solution, brine and dried over anhydrous MgSO$_4$. 3-Chloroperoxybenzoic acid (37 mg, 0.166 mmol) was added and the solution was stirred at rt for 1 h. The solution washed with saturated aqueous NaHCO$_3$ solution, brine and dried over anhydrous MgSO$_4$. The product was purified by reversed-phase HPLC using 10-70% CH$_3$CN/H$_2$O and lyophilized affording the title compound as the corresponding TFA salt. Yield: 34 mg (38%). $^1$H NMR (400 MHz, METHANOL-D$_4$) δ 1.37 (s, 9 H), 1.52-1.58 (m, 2 H), 1.59-1.66 (m, 2 H), 1.69 (s, 9 H), 2.34-2.44 (m, 1 H), 3.36 (m, 2 H), 3.48 (s, 3 H), 3.93 (d, J=3.32 Hz, 1H), 3.95-3.97 (m, 1 H), 4.54 (d, J=7.62 Hz, 2 H), 7.78 (dd, J=9.08, 2.05 Hz, 1 H), 7.92 (d, J=2.15 Hz, 1 H), 7.96 (d, J=9.18 Hz, 1 H); MS (ESI) (M+H)$^+$ 422.0.

Example 10

N-{2-tert-Butyl-1-[(4,4-difluorocyclohexyl)methyl]-1H-benzimidazol-5-yl}-N-methylpropane-1-sulfonamide

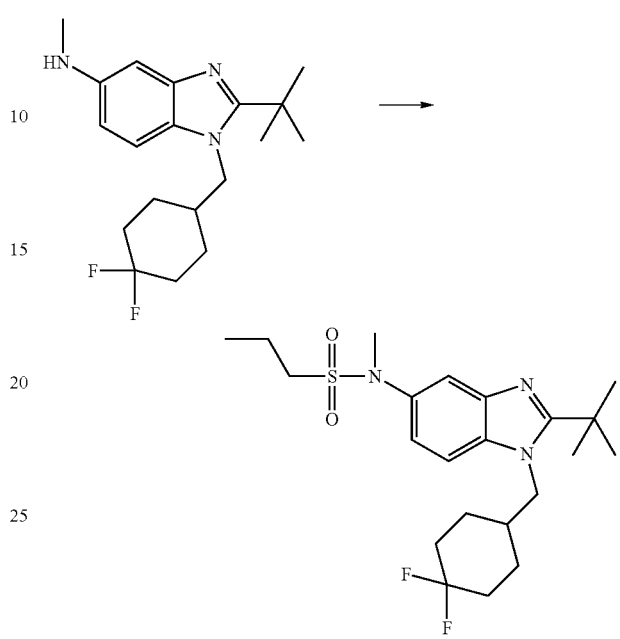

2-tert-Butyl-1-[(4,4-difluorocyclohexyl)methyl]-N-methyl-1H-benzimidazol-5-amine (45 mg, 0.134 mmol) and a catalytic amount of DMAP were dissolved in 3 mL of DCE. Propanesulfonyl chloride (0.020 mL, 0.174 mmol) was added and the solution was stirred at rt for 4 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 55 mg (74%). $^1$H NMR (400 MHz, METHANOL-D$_4$) δ 1.00 (t, J=7.42 Hz, 3 H), 1.51-1.60 (m, 2 H), 1.66 (s, 9 H), 1.68-1.73 (m, 2 H), 1.73-1.81 (m, 4 H), 2.00-2.11 (m, 2 H), 2.18-2.29 (m, 1 H) 3.06-3.12 (m, 2 H), 3.38 (s, 3 H), 4.54 (d, J=7.62 Hz, 2 H), 7.67 (dd, J=9.08, 2.05 Hz, 1 H), 7.79 (d, J=1.56 Hz, 1 H), 7.94 (d, J=8.98 Hz, 1 H); MS (ESI) (M+H)$^-$ 442.0; Anal. Calcd (%) for C$_{22}$H$_{33}$N$_3$O$_2$SF$_2$+1.0 TFA+1.6 H$_2$O: C, 49.32; H, 6.42; N, 7.10. Found: C, 49.39; H, 6.66; N, 6.71.

Example 11

N-{2-tert-Butyl-1-[(4,4-difluorocyclohexyl)methyl]-1H-benzimidazol-5-yl}-N-methylethanesulfonamide

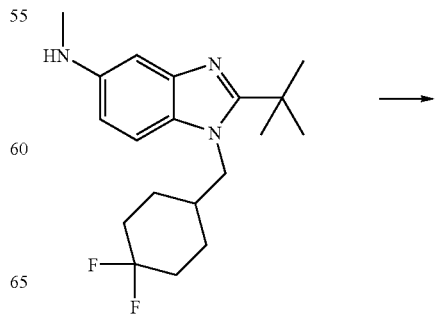

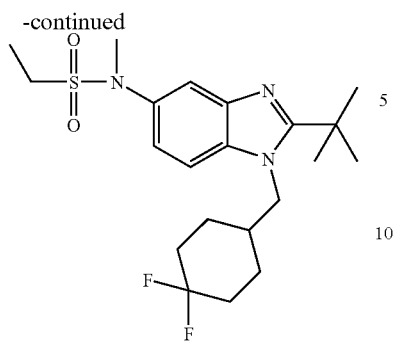

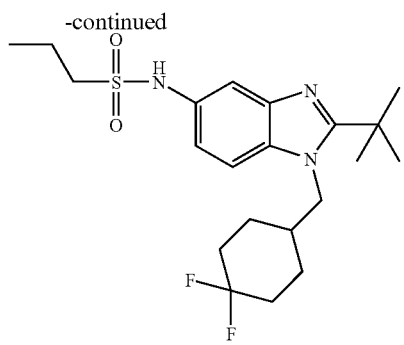

2-tert-Butyl-1-[(4,4-difluorocyclohexyl)methyl]-N-methyl-1H-benzimidazol-5-amine (49 mg, 0.146 mmol) and a catalytic amount of DMAP were dissolved in 3 mL of DCM. Ethanesulfonyl chloride (0.018 mL, 0.190 mmol) was added and the solution was stirred at rt for 12 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 58 mg (73%). $^1$H NMR (600 MHz, MeOD) δ 1.31 (t, J=7.42 Hz, 3 H), 1.34-1.41 (m, 2 H), 1.54-1.62 (m, 2 H), 1.69 (s, 9 H), 1.72-1.80 (m, 2 H), 2.03-2.11 (m, 2 H), 2.33-2.30 (m, 1 H), 3.17 (q, J=7.25 Hz, 2 H), 3.41 (s, 3 H), 4.56 (d, J=7.68 Hz, 2 H), 7.70 (dd, J=8.96, 2.05 Hz, 1 H), 7.82 (d, J=2.05 Hz, 1 H), 7.96 (d, J=8.96 Hz, 1 H); MS (ESI) (M+H)$^+$ 428.0.

2-tert-Butyl-1-[(4,4-difluorocyclohexyl)methyl]-1H-benzimidazol-5-amine (for preparation, see the following steps B to E) (45 mg, 0.140 mmol) and a catalytic amount of DMAP were dissolved in 3 mL of DCM. Propanesulfonyl chloride (0.020 mL, 0.182 mmol) was added and the solution was stirred at rt for 4 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 39 mg (51%). $^1$H NMR (600 MHz, CD$_3$OD) δ 1.00 (t, J=7.55 Hz, 3 H), 1.53-1.61 (m, 2 H), 1.67 (s, 9 H), 1.70-1.77 (m, 3 H), 1.77-1.85 (m, 3 H), 2.02-2.11 (m, 2 H), 2.22-2.29 (m, 1 H), 3.08-3.13 (m, 2 H), 4.53 (d, J=7.42 Hz, 2 H), 7.41 (dd, J=9.09, 1.92 Hz, 1 H), 7.75 (d, J=1.79 Hz, 1 H), 7.89 (d, J=9.22 Hz, 1 H); MS (ESI) (M+H)$^+$ 428.0.

Example 12

N-{2-tert-Butyl-1-[(4,4-difluorocyclohexyl)methyl]-1H-benzimidazol-5-yl}propane-1-sulfonamide

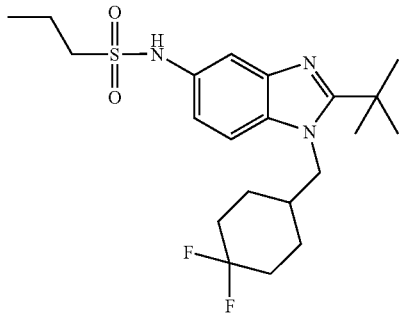

Step A: N-{2-tert-Butyl-1-[(4,4-difluorocyclohexyl)methyl]-1H-benzimidazol-5-yl}propane-1-sulfonamide

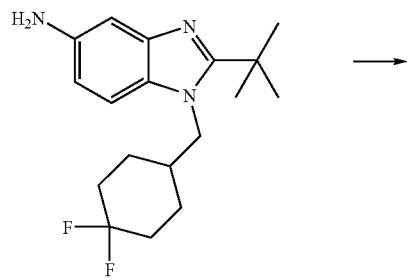

Step B: N-(4-{[(4,4-Difluorocyclohexyl)methyl]amino}-3-nitrophenyl)acetamide

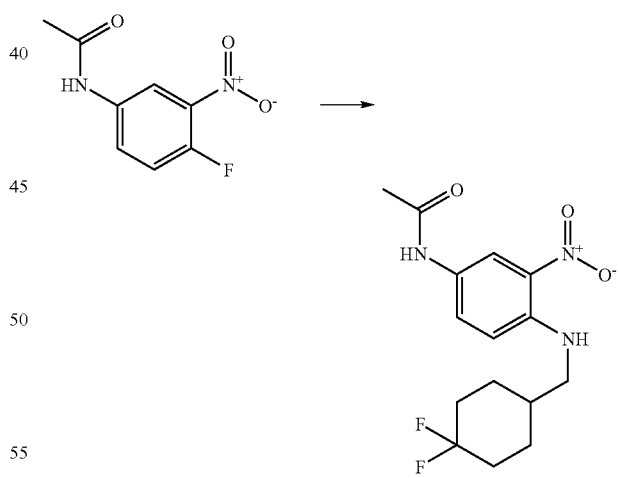

N-(4-Fluoro-3-nitrophenyl)acetamide (1.15 g, 5.84 mmol) and [(4,4-difluorocyclohexyl)methyl]amine hydrochloride (1.30 g, 7.59 mmol) were stirred in 30 mL of EtOH containing TEA (2.40 mL, 17.5 mmol) at 80° C. for 48 h. The solvent was evaporated. The residue was dissolved in EtOAc and washed with aqueous 5% KHSO$_4$ solution, saturated aqueous NaHCO$_3$ solution, saturated aqueous NaCl solution and dried over anhydrous Na$_2$SO$_4$. The product was crystallized from EtOAc. The left over mother liquor was purified by silica gel flash chromatography using 2:1/hexanes:acetone as eluent.

Yield: 1.50 g (78%). $^1$H NMR (400 MHz, CHLOROFORM-D) δ 1.33-1.47 (m, 2 H), 1.66-1.77 (m, 2 H), 1.77-1.86 (m, 1 H), 1.89-1.93 (m, 1 H), 1.93-1.97 (m, 1 H), 2.10-2.17 (m, 2 H), 2.18 (s, 3 H), 3.23 (dd, J=6.74, 5.76 Hz, 2 H), 6.83 (d, J=9.37 Hz, 1 H), 7.15 (s, 1 H), 7.80 (dd, J=9.18, 2.54 Hz, 1 H), 8.09 (d, J=2.54 Hz, 2 H).

Step C: N-(3-Amino-4-{[(4,4-difluorocyclohexyl)methyl]amino}phenyl)acetamide

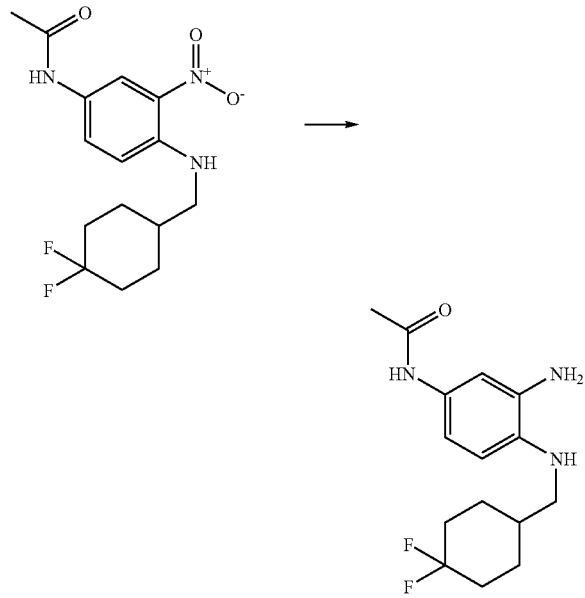

N-(4-{[(4,4-Difluorocyclohexyl)methyl]amino}-3-nitrophenyl)acetamide (1.48 g, 4.52 mmol) was dissolved in 50 mL of EtOAc containing a catalytic amount of 10% Pd/C. The solution was shaken in a Parr hydrogenation apparatus under H$_2$ atmosphere (45 psi) at rt for 24 h. The solution was filtered through Celite and the solvent was evaporated. Yield: 1.32 g (98%). $^1$H NMR (400 MHz, CHLOROFORM-D) δ 1.31-1.43 (m, 2 H), 1.64-1.73 (m, 2 H), 1.74-1.82 (m, 1 H), 1.89-1.93 (m, 1 H), 1.93-1.96 (m, 1 H), 2.08-2.17 (m, 5 H), 3.00 (d, J=6.64 Hz, 2 H), 3.27-3.46 (m, 2 H), 6.55 (d, J=8.40 Hz, 1 H), 6.70 (dd, J=8.40, 2.34 Hz, 1 H), 7.01 (s, 1 H), 7.13 (d, J=2.34 Hz, 1 H).

Step D: N-{2-tert-Butyl-1-[(4,4-difluorocyclohexyl)methyl]-1H-benzimidazol-5-yl}acetamide

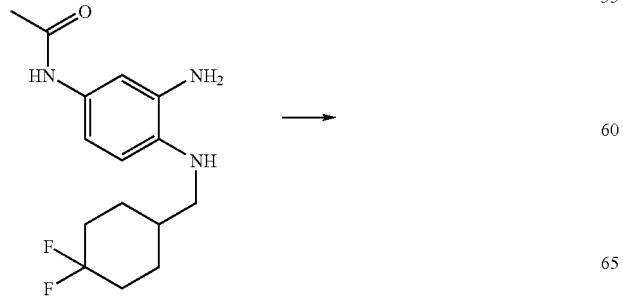

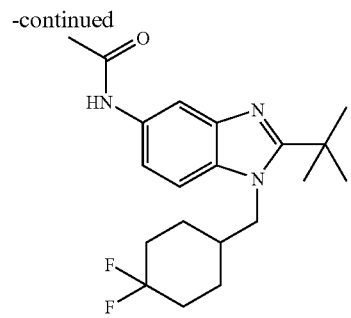

N-(3-Amino-4-{[(4,4-difluorocyclohexyl)methyl]amino}phenyl) acetamide (1.32 g, 4.44 mmol) was dissolved in 100 mL of DCM containing DMAP (108 mg, 0.89 mmol). Trimethylacetyl chloride (0.60 mL, 4.88 mmol) was added dropwise and the solution was stirred at rt for 2 h. The solution was washed with saturated aqueous NaHCO$_3$ solution, saturated aqueous NaCl solution and dried over anhydrous Na$_2$SO$_4$. Part of the product precipitated during the washings and was filtered. The organic phase was evaporated and combined with the precipitate. The product was dissolved in 30 mL of AcOH and placed in 6 sealed tubes (5 mL/tube). Each tube was heated at 150° C. in a Personal Chemistry microwaves instrument for 2.5 h. The fractions were pooled and the solvent was evaporated. The product was dissolved in EtOAc and washed with aqueous NaHCO$_3$ solution, saturated aqueous NaCl solution and dried over anhydrous Na$_2$SO$_4$. The product was purified by silica gel flash chromatography using 2:1/acetone:hexanes as eluent. Yield: 1.11 g (68%). $^1$H NMR (400 MHz, METHANOL-D$_4$) δ 1.40-1.49 (m, 2 H), 1.52 (s, 9 H), 1.60-1.65 (m, 2 H), 1.67-1.77 (m, 1 H), 1.96-2.06 (m, 3 H), 2.11 (s, 3 H), 2.15-2.23 (m, 1 H), 4.28 (d, J=7.62 Hz, 2 H), 7.35-7.39 (m, 1 H), 7.40-7.44 (m, 1 H), 7.85 (d, J=1.76 Hz, 1 H).

Step E: 2-tert-Butyl-1-[(4,4-difluorocyclohexyl)methyl]-1H-benzimidazol-5-amine

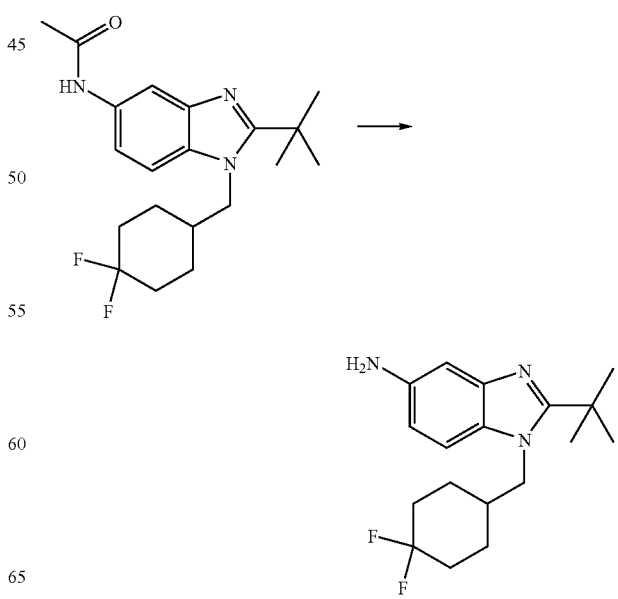

N-{2-tert-Butyl-1-[(4,4-difluorocyclohexyl)methyl]-1H-benzimidazol-5-yl}acetamide (500 mg, 1.37 mmol) was dissolved in 10 mL of 1:1/EtOH:2M HCl. The solution was divided into two sealed tubes (5 mL/tube). Each tube was heated at 120° C. in a Personal Chemistry microwaves instrument for 1 h. The fractions were pooled and the solvent was evaporated. The residue was diluted with 2M NaOH and extracted (3×) with EtOAc. The organic phase was washed with saturated aqueous NaCl solution and dried over anhydrous $Na_2SO_4$. The solvent was evaporated. Yield: 440 mg (99%). $^1$H NMR (400 MHz, CHLOROFORM-D) δ 1.40-1.52 (m, 2 H), 1.52-1.54 (m, 9 H), 1.56-1.66 (m, 4 H), 1.68-1.75 (m, 2 H), 2.07-2.17 (m, 3 H), 4.14 (d, J=7.62 Hz, 2 H), 6.65 (dd, J=8.50, 2.25 Hz, 1 H), 7.04-7.09 (m, 2 H).

Example 13

N-{2-tert-Butyl-1-[(4,4-difluorocyclohexyl)methyl]-1H-benzimidazol-5-yl}methanesulfonamide

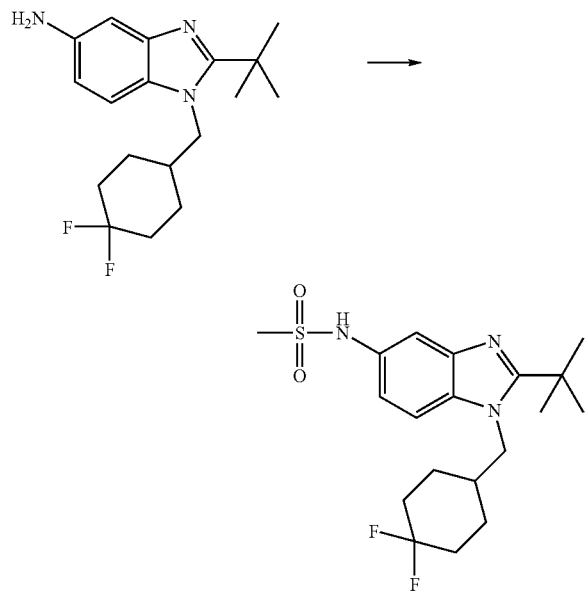

2-tert-Butyl-1-[(4,4-difluorocyclohexyl)methyl]-1H-benzimidazol-5-amine (40 mg, 0.124 mmol) and a catalytic amount of DMAP were dissolved in 3 mL of DCM. Methanesulfonyl chloride (0.012 mL, 0.149 mmol) was added and the solution was stirred at rt for 2 h. The solution was washed with saturated aqueous $NaHCO_3$ solution, brine and dried over anhydrous $MgSO_4$. The solvent was evaporated and the product was purified by reversed-phase HPLC using 10-70% $CH_3CN/H_2O$ and lyophilized affording the title compound as the corresponding TFA salt. Yield: 50 mg (79%). $^1$H NMR (600 MHz, MeOD) δ 1.53-1.61 (m, 2 H), 1.67 (s, 9 H), 1.71-1.76 (m, 3 H), 1.76-1.82 (m, 1 H), 2.04-2.11 (m, 2 H), 2.23-2.29 (m, 1 H), 3.01 (s, 3 H), 4.54 (d, J=7.68 Hz, 2 H), 7.42 (dd, J=9.22, 2.05 Hz, 1 H), 7.75 (d, J=1.79 Hz, 1 H), 7.91 (d, J=8.96 Hz, 1 H); MS (ESI) (M+H)+ 400.0; Anal. Calcd (%) for $C_{19}H_{27}N_3O_2SF_2$+1.9 TFA+0.1 $H_2O$: C, 44.32; H, 4.75; N, 6.80. Found C, 44.34; H, 4.78; N, 6.55.

Example 14

N-{2-tert-Butyl-1-[(4,4-difluorocyclohexyl)methyl]-1H-benzimidazol-5-yl}ethanesulfonamide

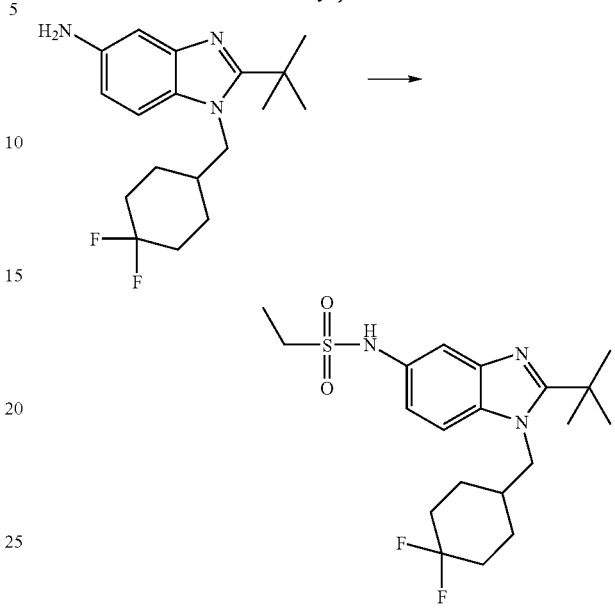

2-tert-Butyl-1-[(4,4-difluorocyclohexyl)methyl]-1H-benzimidazol-5-amine (440 mg, 1.37 mmol) and DMAP (165 mg, 1.37 mmol) were dissolved in 50 mL of DCM. Ethanesulfonyl chloride (0.170 mL, 1.78 mmol) was added dropwise and the solution was stirred at rt for 2.5 h. The solution was washed with saturated aqueous $NaHCO_3$ solution, saturated aqueous NaCl solution and dried over anhydrous $Na_2SO_4$. The product was purified by silica gel flash chromatography using EtOAc as eluent. The fractions were concentrated and the residue was dissolved in 25 mL of MeOH. TFA (0.155 mL, 2.06 mmol) was added dropwise and the solution was stirred at rt for 30 min. The solvent was evaporated and the product was precipitated in ether affording the title compound as its corresponding TFA salt. Yield: 565 mg (78%). $^1$H NMR (400 MHz, METHANOL-$D_4$) δ 1.29 (t, J=7.42 Hz, 3 H), 1.48-1.60 (m, 2 H), 1.64 (s, 9 H), 1.66-1.72 (m, 2 H), 1.73-1.82 (m, 2 H), 1.99-2.09 (m, 2 H), 2.18 (m, 1 H), 3.11 (m, 2 H), 4.50 (d, J=7.62 Hz, 2 H), 7.38 (dd, J=9.08, 2.05 Hz, 1 H), 7.72 (d, J=2.15 Hz, 1 H), 7.85 (d, J=8.98 Hz, 1 H); MS (ESI) (M+H)+ 414.0.

Example 15

N-{2-tert-Butyl-1-[(4,4-difluorocyclohexyl)methyl]-1H-benzimidazol-5-yl}cyclopropanesulfonamide

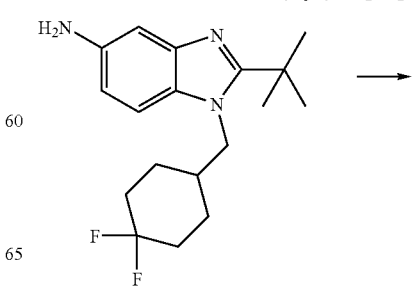

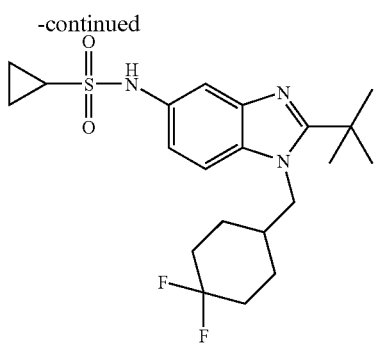

2-tert-Butyl-1-[(4,4-difluorocyclohexyl)methyl]-1H-benzimidazol-5-amine (300 mg, 0.934 mmol) and DMAP (115 mg, 0.934 mmol) were dissolved in 10 mL of DCM. Cyclopropanesulfonyl chloride (170 mg, 1.21 mmol) was added and the solution was stirred at rt for 2 h. The solution was washed with saturated aqueous NaHCO$_3$ solution, brine and dried over anhydrous MgSO$_4$. The product was purified by silica gel flash chromatography using EtOAc as eluent. The fractions were concentrated and the residue was dissolved in 25 mL of MeOH. TFA (0.143 mL, 1.86 mmol) was added dropwise and the solution was stirred at rt for 30 min. The solvent was evaporated and the product was precipitated in ether affording the title compound as its corresponding TFA salt. Yield: 390 mg (77%). $^1$H NMR (400 MHz, METHANOL-D$_4$) δ 0.91-0.97 (m, 2 H), 1.02-1.08 (m, 2 H), 1.48-1.60 (m, 2 H), 1.65 (s, 9 H), 1.67-1.75 (m, 3 H), 1.75-1.82 (m, 1 H), 2.00-2.10 (m, 2 H), 2.18-2.28 (m, 1 H), 2.53-2.61 (m, 1 H), 4.50 (d, J=7.42 Hz, 2 H), 7.42 (dd, J=8.98, 2.15 Hz, 1 H), 7.74 (d, J=1.56 Hz, 1 H), 7.85 (d, J=8.79 Hz, 1 H); MS (ESI) (M+H)$^+$ 426.0; Anal. Calcd (%) for C$_{21}$H$_{29}$N$_3$O$_2$SF$_2$+1.0 TFA; C, 51.20; H, 5.60; N, 7.79. Found: C, 51.38; H, 5.66; N, 7.56.

Example 16

N-{2-tert-Butyl-1-[(4,4-difluorocyclohexyl)methyl]-1H-benzimidazol-5-yl}-N-methylcyclopropanesulfonamide

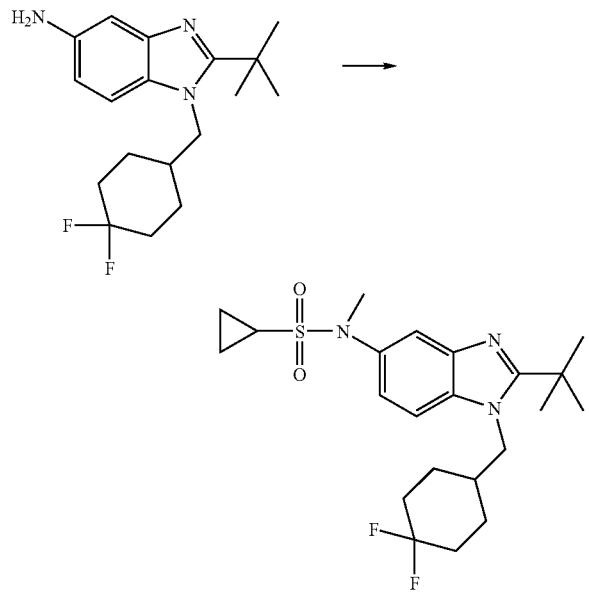

2-tert-Butyl-1-[(4,4-difluorocyclohexyl)methyl]-1H-benzimidazol-5-amine (65 mg, 0.202 mmol) and a catalytic amount of DMAP were dissolved in 5 mL of DCM. Cyclopropanesulfonyl chloride (34 mg, 0.242 mmol) was added and the solution was stirred at rt for 6 h. The solution was washed with saturated aqueous NaHCO$_3$ solution, brine and dried over anhydrous MgSO$_4$. The solvent was evaporated. The residue was dissolved in 5 mL of DMF at 0° C. and NaH (12 mg, 0.303 mmol) was added. The solution was stirred at 0° C. for 15 min. Methyl iodide (0.025 mL, 0.404 mmol) was added and the solution was stirred at rt for 2 h. The reaction was quenched with saturated aqueous NaHCO$_3$ solution and the solvent was evaporated. The product was dissolved in EtOAc and washed with aqueous NaHCO$_3$ solution, saturated aqueous NaCl solution and dried over anhydrous Na$_2$SO$_4$. The solvent was evaporated and the product was purified by reversed-phase HPLC using 10-70% CH$_3$CN/H$_2$O and lyophilized affording the title compound as the corresponding TFA salt. Yield: 60 mg (54%). $^1$H NMR (600 MHz, CD$_3$OD) δ 0.90-0.94 (m, 2 H), 0.97-1.01 (m, 2 H), 1.54-1.62 (m, 2 H), 1.68 (s, 9 H), 1.73-1.81 (m, 4 H), 2.03-2.11 (m, 2 H), 2.23-2.30 (m, 1 H), 2.59-2.65 (m, 1 H), 3.43 (s, 3 H), 4.56 (d, J=7.68 Hz, 2 H), 7.72 (d, J=9.47 Hz, 1 H), 7.81 (s, 1 H), 7.95 (d, J=8.96 Hz, 1 H); MS (ESI) (M+H)$^+$ 440.0.

Example 17

N-{2-tert-Butyl-1-[(4,4-difluorocyclohexyl)methyl]-1H-benzimidazol-5-yl}-2-methylpropane-2-sulfonamide

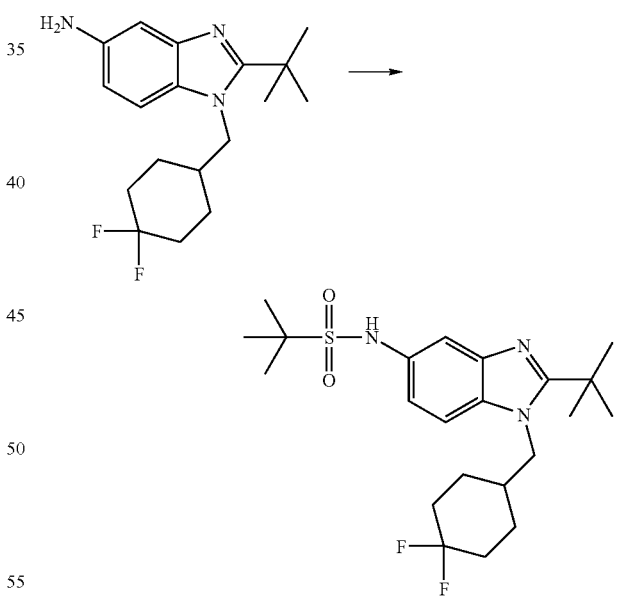

2-tert-Butyl-1-[(4,4-difluorocyclohexyl)methyl]-1H-benzimidazol-5-amine (66 mg, 0.205 mmol) and DMAP (25 mg, 0.205 mmol) were dissolved in 5 mL of DCM. t-Butylsulfinyl chloride (0.031 mL, 0.246 mmol) was added and the solution was stirred at rt for 2 h. The solution was washed with saturated aqueous NaHCO$_3$ solution, brine and dried over anhydrous MgSO$_4$. 3-Chloroperoxybenzoic acid (90 mg, 0.410 mmol) was added and the solution was stirred at rt for 12 h. The solution was washed with saturated aqueous NaHCO$_3$ solution, brine and dried over anhydrous MgSO$_4$. The product was purified by reversed-phase HPLC using 10-70% CH$_3$CN/H$_2$O and lyophilized affording the title compound as the corresponding TFA salt. Yield: 55 mg (48%). $^1$H NMR (400 MHz, METHANOL-D$_4$) δ 1.35 (s, 9 H), 1.49-1.60 (m, 2 H), 1.64 (s, 9 H), 1.68-1.75 (m, 3 H), 1.76-1.82 (m, 1 H), 2.00-2.09 (m, 2 H), 2.19-2.28 (m, 1 H), 4.50 (d, J=7.42 Hz, 2 H), 7.42 (dd, J=9.08, 2.05 Hz, 1 H), 7.81-7.86 (m, 2 H); MS (ESI) (M+H)$^+$ 442.0; Anal. Calcd (%) for C$_{22}$H$_{33}$N$_3$O$_2$SF$_2$+1.2 TFA+0.2 H$_2$O; C, 50.35; H, 5.99; N, 7.22. Found C, 50.36; H, 5.73; N, 7.08.

Example 18

N-[1-[(4,4-Difluorocyclohexyl)methyl]-2-(1,1-difluoroethyl)-1H-benzimidazol-5-yl]cyclopropanesulfonamide

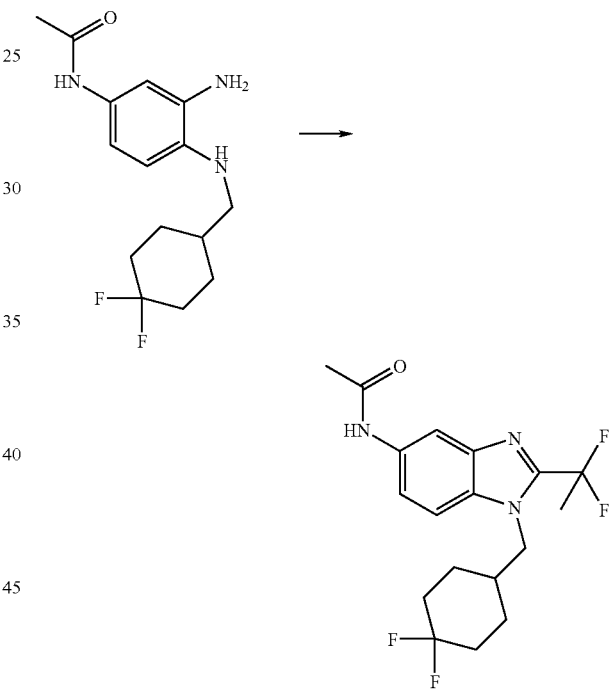

Step A: N-[1-[(4,4-Difluorocyclohexyl)methyl]-2-(1,1-difluoroethyl)-1H-benzimidazol-5-yl]cyclopropanesulfonamide

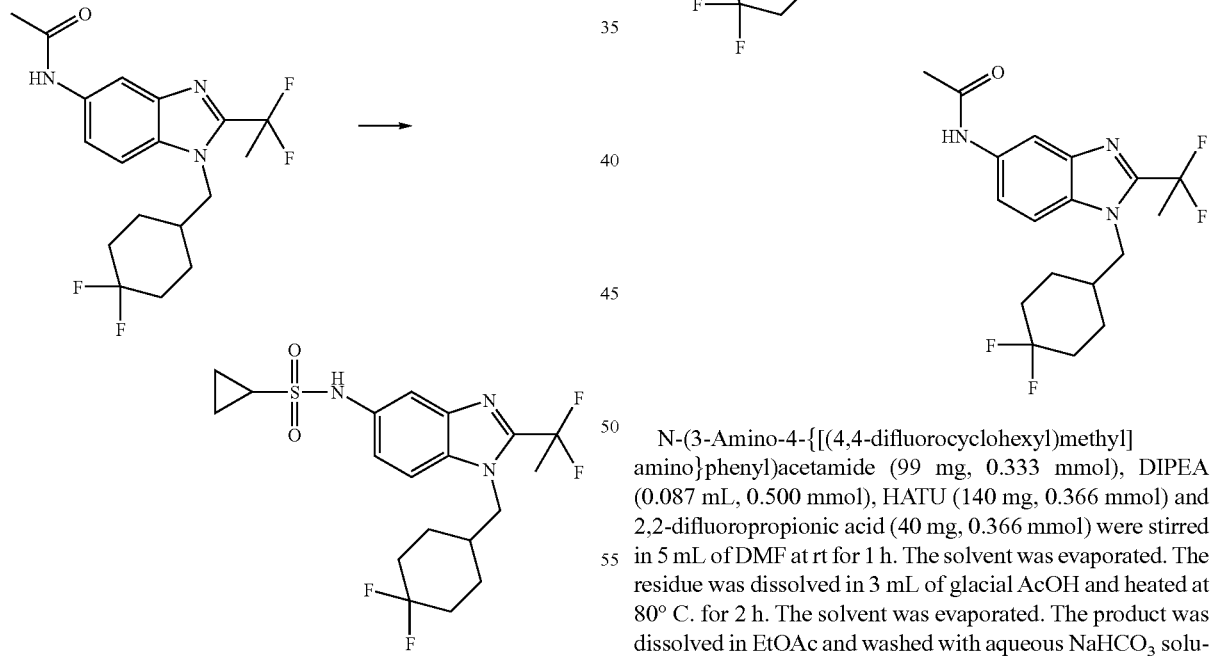

N-[1-[(4,4-Difluorocyclohexyl)methyl]-2-(1,1-difluoroethyl)-1H-benzimidazol-5-yl]acetamide (for preparation see the following step B) (95 mg, 0.256 mmol) was heated in 5 mL of 1:1/2M HCl:EtOH at 120° C. for 1 h using a Personal Chemistry microwaves instrument. The solvent was evaporated. The residue was basified with 2M NaOH and extracted (3×) with EtOAc. The organic phase was washed with saturated aqueous NaCl solution and dried over anhydrous Na$_2$SO$_4$. The solvent was evaporated. The product was dissolved in 5 mL of DCM containing DMAP (31 mg, 0.256 mmol) and cyclopropanesulfonyl chloride (53 mg, 0.384 mmol) was added. The solution was stirred at rt for 3 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 35 mg (25%). $^1$H NMR (400 MHz, METHANOL-D$_4$) δ 0.88-0.95 (m, 2 H), 0.98-1.03 (m, 2 H), 1.39-1.51 (m, 2 H), 1.61-1.68 (m, 3 H), 1.70-1.79 (m, 1 H), 2.03 (s, 2 H), 2.15 (s, 1 H), 2.23 (m, 3 H), 2.47-2.55 (m, 1 H), 4.35 (d, J=7.62 Hz, 2 H), 7.39 (dd, J=8.79, 1.95 Hz, 1 H), 7.65 (d, J=8.79 Hz, 1 H), 7.67 (d, J=2.15 Hz, 1 H); MS (ESI) (M+H)$^+$ 434.0; Anal. Calcd (%) for C$_{19}$H$_{23}$N$_3$O$_2$SF$_4$+0.7 TFA; C, 47.74; H, 4.65; N, 8.19. Found: C, 47.88; H, 4.68; N, 8.19.

Step B: N-[1-[(4,4-Difluorocyclohexyl)methyl]-2-(1,1-difluoroethyl)-1H-benzimidazol-5-yl]acetamide

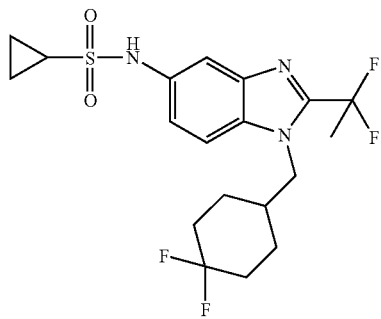

N-(3-Amino-4-{[(4,4-difluorocyclohexyl)methyl] amino}phenyl)acetamide (99 mg, 0.333 mmol), DIPEA (0.087 mL, 0.500 mmol), HATU (140 mg, 0.366 mmol) and 2,2-difluoropropionic acid (40 mg, 0.366 mmol) were stirred in 5 mL of DMF at rt for 1 h. The solvent was evaporated. The residue was dissolved in 3 mL of glacial AcOH and heated at 80° C. for 2 h. The solvent was evaporated. The product was dissolved in EtOAc and washed with aqueous NaHCO$_3$ solution, saturated aqueous NaCl solution and dried over anhydrous Na$_2$SO$_4$. The product was purified by silica gel flash chromatography using EtOAc as eluent. Yield: 100 mg (81%). $^1$H NMR (400 MHz, CHLOROFORM-D) δ 1.39-1.52 (m, 2 H), 1.57-1.63 (m, 1 H), 1.64-1.71 (m, 3 H), 2.06-2.16 (m, 3 H), 2.22 (s, 3 H), 2.29 (m, 3 H), 4.25 (d, J=7.42 Hz, 2 H), 7.31 (s, 1 H), 7.35 (d, J=8.79 Hz, 1 H), 7.60 (dd, J=8.89, 1.86 Hz, 1 H), 7.86 (d, J=1.76 Hz, 1 H).

Example 19

N-[1-[(4,4-Difluorocyclohexyl)methyl]-2-(1,1-difluoroethyl)-1H-benzimidazol-5-yl]ethanesulfonamide

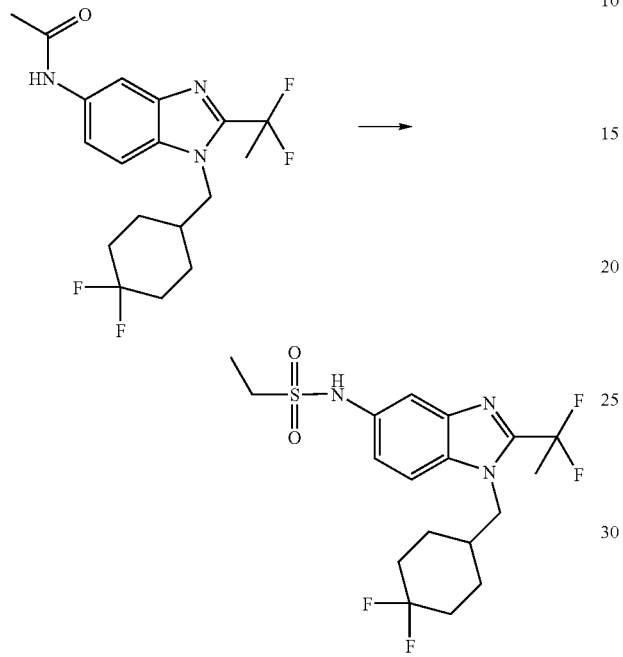

N-[1-[(4,4-Difluorocyclohexyl)methyl]-2-(1,1-difluoroethyl)-1H-benzimidazol-5-yl]acetamide (80 mg, 0.215 mmol) was heated in 5 mL of 1:1/2M HCl: EtOH at 120° C. for 1 h using a Personal Chemistry microwaves instrument. The solvent was evaporated. The residue was basified with 2M NaOH and extracted (3×) with EtOAc. The organic phase was washed with saturated aqueous NaCl solution and dried over anhydrous $Na_2SO_4$. The solvent was evaporated. The product was dissolved in 5 mL of DCM containing DMAP (31 mg, 0.256 mmol) and ethanesulfonyl chloride (0.026 mL, 0.280 mmol) was added. The solution was stirred at rt for 2 h. The solution was washed with saturated aqueous $NaHCO_3$ solution, brine and dried over anhydrous $MgSO_4$. The solvent was evaporated and the product purified by reversed-phase HPLC using 10-70% $CH_3CN/H_2O$ and lyophilized affording the title compound as the corresponding TFA salt. Yield: 22 mg (19%). $^1$H NMR (400 MHz, METHANOL-$D_4$) δ 1.29 (t, J=7.42 Hz, 3 H), 1.36-1.49 (m, 2 H), 1.58-1.66 (m, 3 H), 1.67-1.78 (m, 1 H), 1.96-2.06 (m, 2 H), 2.11-2.15 (m, 1 H), 2.21 (m, 3 H), 3.04 (m, 2 H), 4.33 (d, J=7.62 Hz, 2 H), 7.34 (dd, J=8.98, 1.95 Hz, 1 H), 7.64 (dd, J=5.47, 3.32 Hz, 2 H); MS (ESI) (M+H)$^+$ 421.9; Anal. Calcd (%) for $C_{18}H_{23}N_3O_2SF_4$+0.8 TFA+0.1 $H_2O$: C, 45.76; H, 4.70; N, 8.17. Found C, 45.73; H, 4.52; N, 7.80.

Example 20

N-[1-[(4,4-Difluorocyclohexyl)methyl]-2-(1,1-difluoroethyl)-1H-benzimidazol-5-yl]-2-methylpropane-2-sulfonamide

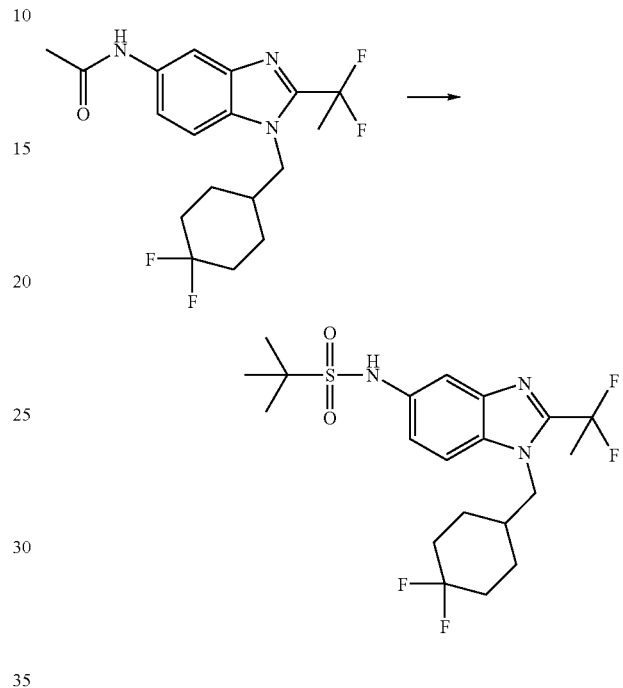

N-[1-[(4,4-Difluorocyclohexyl)methyl]-2-(1,1-difluoroethyl)-1H-benzimidazol-5-yl]acetamide (185 mg, 0.498 mmol) was heated in 5 mL of 1:1/2M HCl: EtOH at 120° C. for 1 h using a Personal Chemistry microwaves instrument. The solvent was evaporated. The residue was basified with 2M NaOH and extracted (3×) with EtOAc. The organic phase was washed with saturated aqueous NaCl solution and dried over anhydrous $Na_2SO_4$. The solvent was evaporated. The residue was dissolved in 5 mL of DCM and t-butylsulfinyl chloride (0.075 mL, 0.598 mmol) and DMAP (25 mg, 0.498 mmol) were added. The solution was stirred at rt for 1 h. The solution was washed with saturated aqueous $NaHCO_3$ solution, brine and dried over anhydrous $MgSO_4$. 3-Chloroperoxybenzoic acid (225 mg, 0.996 mmol) was added and the solution was stirred at rt for 4 h. The solution washed with saturated aqueous $NaHCO_3$ solution, brine and dried over anhydrous $MgSO_4$. The product was purified by reversed-phase HPLC using 10-70% $CH_3CN/H_2O$ and lyophilized affording the title compound as the corresponding TFA salt. Yield: 70 mg (25%). $^1$H NMR (400 MHz, METHANOL-$D_4$) δ 1.33 (s, 9 H), 1.37-1.49 (m, 2 H), 1.60-1.65 (m, 3 H), 1.68-1.78 (m, 1 H), 1.97-2.06 (m, 2 H), 2.11-2.14 (m, 1 H), 2.21 (m, 3 H), 4.32 (d, J=7.62 Hz, 2 H), 7.40 (dd, J=8.89, 2.05 Hz, 1 H), 7.59 (d, J=8.79 Hz, 1 H), 7.70 (d, J=1.95 Hz, 1 H); MS (ESI) (M+H)$^+$ 449.8.

Example 21

N-[2-(1,1-Difluoroethyl)-1-(tetrahydro-2H-pyran-4-ylmethyl)-1H-benzimidazol-5-yl]-N-methylethanesulfonamide

Step A. N-[2-(1,1-difluoroethyl)-1-(tetrahydro-2H-pyran-4-ylmethyl)-1H-benzimidazol-5-yl]-N-methylethanesulfonamide

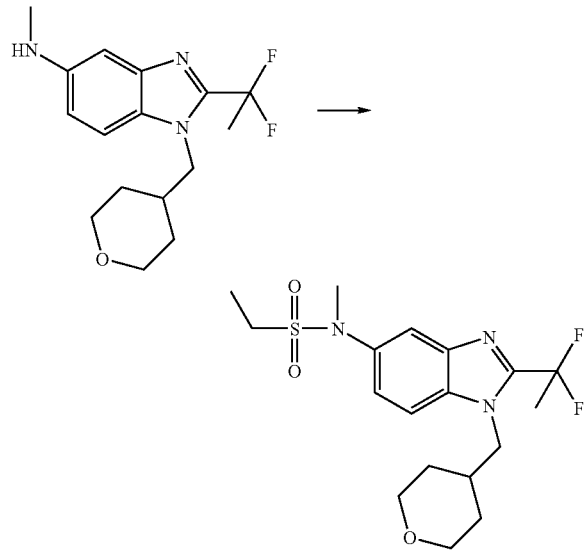

Ethanesulfonyl chloride (55 µL, 0.58 mmol) was added to a solution of 2-(1,1-difluoroethyl)-N-methyl-1-(tetrahydro-2H-pyran-4-ylmethyl)-1H-benzimidazol-5-amine (150 mg, 0.48 mmol) and DMAP (71 mg, 0.58 mmol) in DCM (15 mL) at ambient temperature. The reaction mixture was stirred overnight and the solvent was concentrated. The product was purified by reverse-phase preparative HPLC using MeCN 10 to 90% gradient in water to provide the TFA salt of the title compound as white solid. Yield: 70 mg (28%); $^1$H NMR (400 MHz, CD$_3$OD) δ 1.24-1.37 (m, 3 H), 1.36-1.53 (m, 4 H), 2.12-2.32 (m, 3 H), 3.05-3.17 (m, 2 H), 3.25-3.31 (m, 2 H), 3.33 (d, J=3.71 Hz, 1 H), 3.36 (s, 2 H), 3.89 (m, 2 H), 4.33 (d, J=7.42 Hz, 2 H), 7.49 (dd, J=8.79, 1.95 Hz, 1 H), 7.69 (d, J=8.98 Hz, 1 H), 7.77 (d, J=1.76 Hz, 1 H); MS (ESI) (M+H)$^-$ 402.0;

Step B. N-{5-[Acetyl(methyl)amino]-2-[(tetrahydro-2H-pyran-4-ylmethyl)amino]phenyl}-2,2-difluoropropanamide

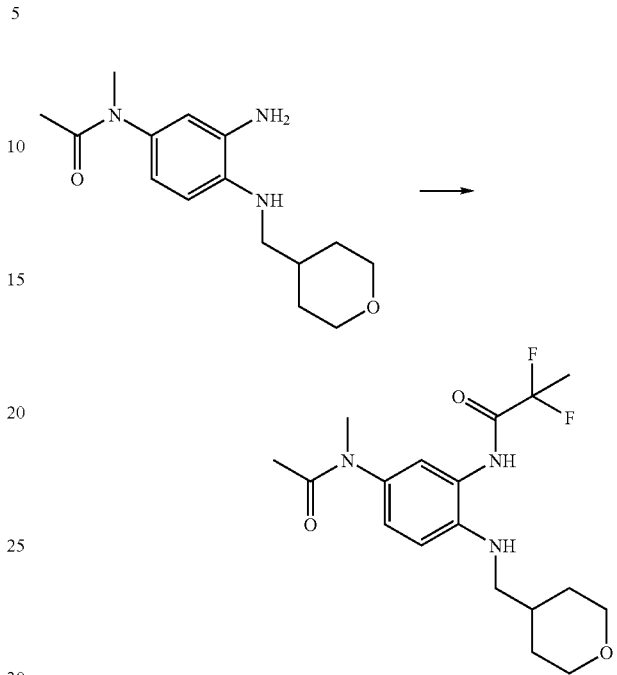

HATU (1.44 g, 3.78 mmol) and N-{3-amino-4-[(tetrahydro-2H-pyran-4-ylmethyl)amino]phenyl}-N-methylacetamide (1.00 g, 3.60 mmol) (for preparation, see Example 1, steps B to E) were added to a solution of 2,2-difluoropropanoic acid (0.40 g, 3.60 mmol) and DIPEA (0.75 mL, 4.32 mmol) in DMF (100 mL) at room temperature. The reaction mixture was stirred overnight. The solvent was concentrated and the crude product was recovered in EtOAc. The organic was washed with water, saturated NaHCO$_3$ solution and brine. The organic layer was dried over anhydrous Na$_2$SO$_4$ and filtered. The solvent was concentrated giving the title compound that was used for the next step without further purification. Yield: 1.00 g (75%); MS (ESI) (M+H)$^+$: 370.2.

Step C. N-[2-(1,1-Difluoroethyl)-1-(tetrahydro-2H-pyran-4-ylmethyl)-1H-benzimidazol-5-yl]-N-methylacetamide

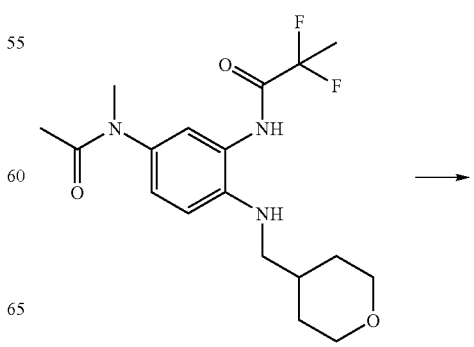

-continued

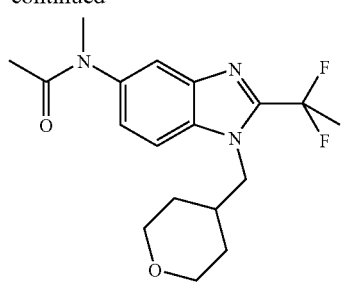

N-{5-[Acetyl(methyl)amino]-2-[(tetrahydro-2H-pyran-4-ylmethyl)amino]phenyl}-2,2-difluoropropanamide (1.00 g, 2.70 mmol) was heated to 90° C. overnight in acetic acid (20 mL). The solvent was concentrated. The crude product was purified by flash chromatography on silica gel, using MeOH 3.5% and acetone 8% in DCM as eluent, giving the title compound. Yield: 0.48 g (50%); MS (ESI) (M+H)$^+$: 352.0.

Step D. 2-(1,1-difluoroethyl)-N-methyl-1-(tetrahydro-2H-pyran-4-ylmethyl)-1H-benzimidazol-5-amine

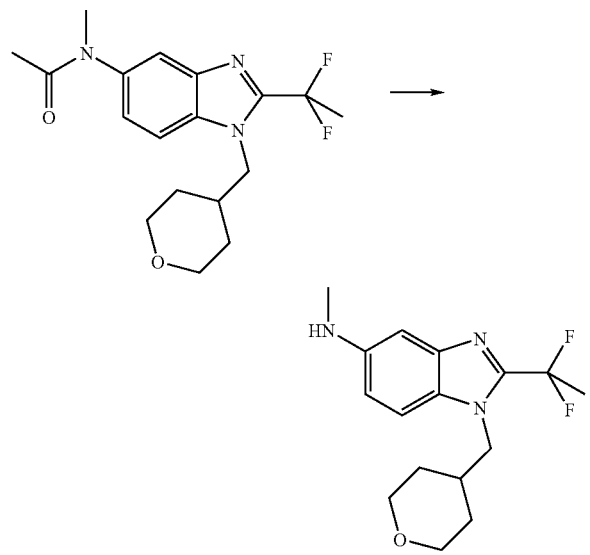

N-[2-(1,1-Difluoroethyl)-1-(tetrahydro-2H-pyran-4-ylmethyl)-1H-benzimidazol-5-yl]-N-methylacetamide (0.48 g, 1.37 mmol) was heated to 80° C. overnight in concentrated HCl (80 mL). The reaction mixture was cool to 0° C. and brought to slightly basic pH using NaOH solution. The compound was extracted with EtOAc (3×) and the combined organic layers were washed with brine, dried over anhydrous Na$_2$SO$_4$ and filtered. The solvent was concentrated giving the title compound that was used for the next step without further purification. Yield: 0.42 g (98%); MS (ESI) (M+H)$^+$: 310.2.

Example 22

N-[2-(1,1-Difluoroethyl)-1-(tetrahydro-2H-pyran-4-ylmethyl)-1H-benzimidazol-5-yl]-N-methylpropane-1-sulfonamide

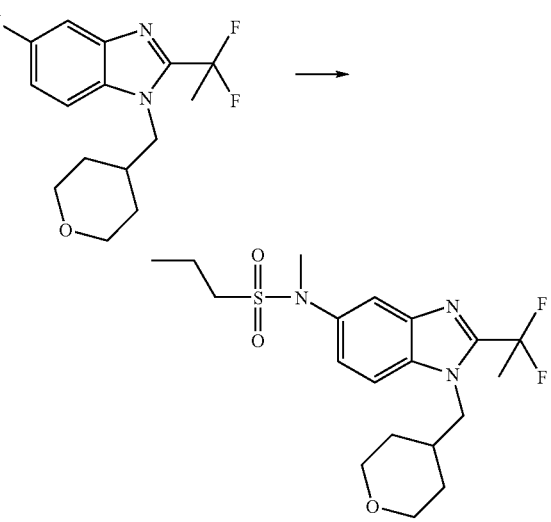

Following the procedure of step A in example 21 and using propanesulfonyl chloride (65 μL, 0.58 mmol) provided the TFA salt of the title compound as a white solid. Yield: 68 mg (26%); $^1$H NMR (400 MHz, CD$_3$OD) δ 1.02 (t, J=7.42 Hz, 3 H), 1.40-1.54 (m, 4 H), 1.74-1.87 (m, 1 H), 2.17-2.34 (m, 3 H), 3.05-3.15 (m, 2 H), 3.32-3.37 (m, 2 H), 3.37 (s, 3 H), 3.85-3.97 (m, 2 H), 4.35 (d, J=7.62 Hz, 2 H), 7.50 (dd, J=8.89, 2.05 Hz, 1 H), 7.71 (d, J=8.79 Hz, 1 H), 7.78 (d, J=1.95 Hz, 1 H); MS (ESI) (M+H)$^+$ 416.0; Anal. Calcd for C$_{19}$H$_{27}$F$_2$N$_3$O$_3$S+0.1 MeCN: C, 54.96; H, 6.56; N 10.35. Found: C, 55.02; H, 6.40; N, 10.24.

Example 23

N-[2-(1,1-Difluoroethyl)-1-(tetrahydro-2H-pyran-4-ylmethyl)-1H-benzimidazol-5-yl]-N-methylcyclopropanesulfonamide

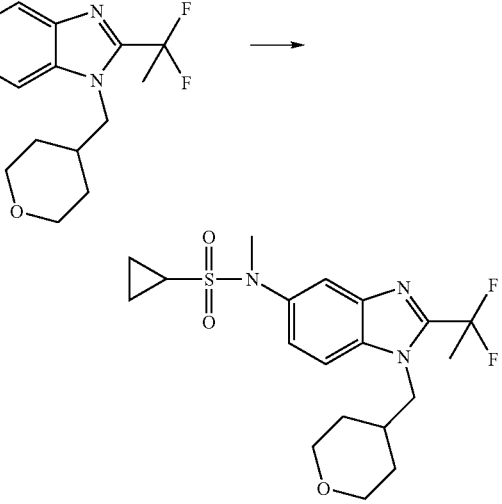

Following the procedure of step A in example 21 using cyclopropanesulfonyl chloride (81 μL, 0.58 mmol) and heating to 60° C. overnight, provided the TFA salt of the title compound as a white solid. Yield: 135 mg (52%); $^1$H NMR (400 MHz, CD$_3$OD) δ 0.85-0.93 (m, 2 H), 0.93-1.03 (m, 2 H), 1.39-1.55 (m, 4 H), 2.24 (m, 3 H), 2.55-2.66 (m, 1 H), 3.31-3.38 (m, 3 H), 3.39 (s, 3 H), 3.86-3.97 (m, 2 H), 4.36 (d, J=7.42 Hz, 2 H), 7.52 (dd, J=8.79, 2.15 Hz, 1 H), 7.70 (d, J=8.79 Hz, 1 H), 7.81 (d, J=2.15 Hz, 1 H); MS (ESI) (M+H)$^+$ 414.0; Anal. Calcd for C$_{19}$H$_{25}$F$_2$N$_3$O$_3$S+0.1 H$_2$O: C, 54.95; H, 6.12; N, 10.12. Found: C, 54.91; H, 6.09; N, 9.68.

Example 24

N-{2-tert-Butyl-1-[(4-fluorocyclohexyl)methyl]-1H-benzimidazol-5-yl}ethanesulfonamide

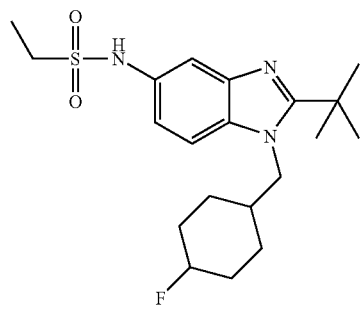

Step A: N-{2-tert-Butyl-1-[(4-fluorocyclohexyl)methyl]-1H-benzimidazol-5-yl}ethanesulfonamide

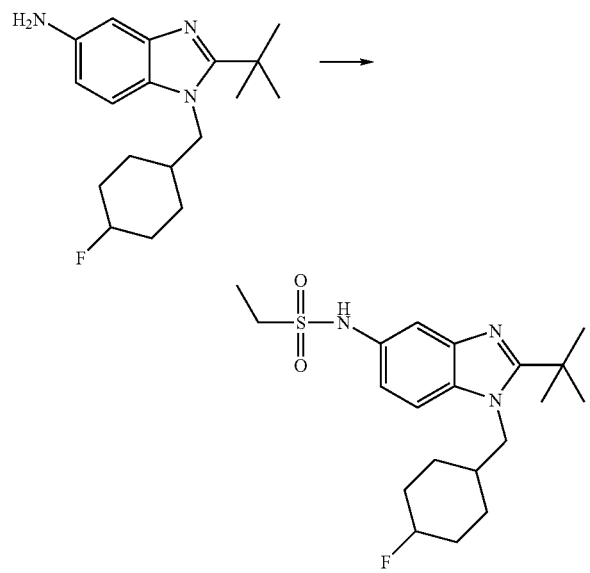

2-tert-Butyl-1-[(4-fluorocyclohexyl)methyl]-1H-benzimidazol-5-amine (for preparation see following steps B to F) (60 mg, 0.198 mmol) and DMAP (24 mg, 0.198 mmol) were dissolved in 5 mL of DCM. Ethanesulfonyl chloride (0.025 mL, 0.257 mmol) was added and the solution was stirred at rt for 2 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 50 mg (50%). $^1$H NMR (400 MHz, METHANOL-D$_4$) δ 1.29 (t, J=7.42 Hz, 3 H), 1.34-1.41 (m, 2 H), 1.43-1.51 (m, 1 H), 1.53-1.62 (m, 1 H), 1.63-1.66 (m, 9 H), 1.69-1.75 (m, 2 H), 1.96-2.04 (m, 1 H), 2.06-2.12 (m, 2 H), 3.12 (q, J=7.42 Hz, 2 H), 4.44-4.49 (m, 2 H), 7.39 (dd, J=9.08, 2.05 Hz, 1 H), 7.73 (d, J=2.15 Hz, 1 H), 7.85 (d, J=9.18 Hz, 0.7 H), 7.85-7.88 (d, J=9.18 Hz, 0.3H); MS (ESI) (M+H)$^+$ 396.0; Anal. Calcd (%) for C$_{20}$H$_{30}$N$_3$O$_2$SF+1.3 TFA+0.5 H$_2$O: C, 49.11; H, 5.89; N, 7.60. Found: C, 49.10; H, 5.84; N, 7.52.

Step B: tert-Butyl[(4-fluorocyclohex-3-en-1-yl)methyl]carbamate

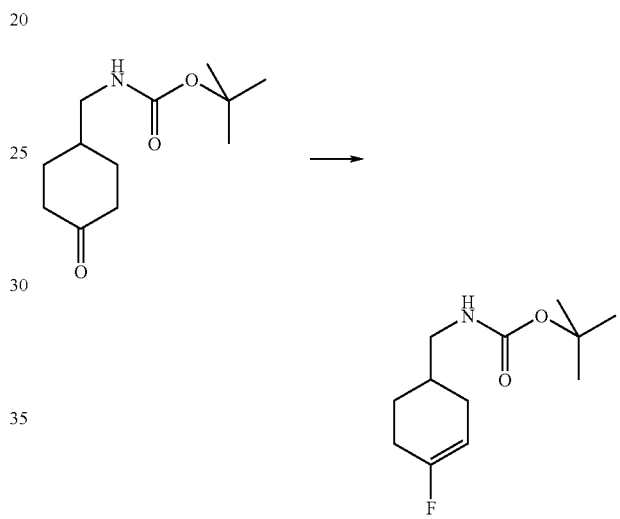

4-N-Boc-aminomethyl cyclohexanone (4.95 g, 21.8 mmol) was dissolved in 80 mL of THF. DAST (4.3 mL, 32.7 mmol) was added dropwise and the solution was stirred at 50° C. for 5 h. The solvent was concentrated and the product purified by silica gel flash chromatography using 3:1/hexanes:EtOAc as eluent. Yield: 1.62 g (30%). $^1$H NMR (400 MHz, CHLOROFORM-D) δ 1.36-1.42 (m, 1 H), 1.44 (s, 9 H), 1.70-1.80 (m, 2 H), 1.82-1.90 (m, 1 H), 2.09-2.17 (m, 1 H), 2.17-2.29 (m, 2 H), 3.04-3.11 (m, 2 H), 4.61 (s, 1 H), 5.11-5.15 (m, 0.5 H), 5.16-5.19 (m, 0.5 H).

Step C: [(4-Fluorocyclohex-3-en-1-yl)methyl]amine hydrochloride

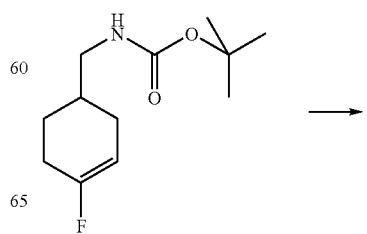

-continued

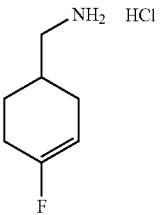

tert-Butyl [(4-fluorocyclohex-3-en-1-yl)methyl]carbamate (1.62 g, 7.06 mmol) was stirred in 25 mL of 1M HCl/AcOH at rt for 2 h. The solvent was evaporated and the product was precipitated in ether, filtered and dried under vacuum. Yield: 1.13 g (97%). $^1$H NMR (400 MHz, METHANOL-D$_4$) δ 1.44-1.53 (m, 1 H), 1.80-1.89 (m, 2 H), 1.90-1.98 (m, 1 H), 2.16-2.23 (m, 2 H), 2.26-2.34 (m, 1 H), 2.88 (d, J=6.25 Hz, 2 H), 5.12-5.19 (m, 1 H).

Step C: N-(4-{[(4-Fluorocyclohex-3-en-1-yl)methyl]amino}-3-nitrophenyl)acetamide

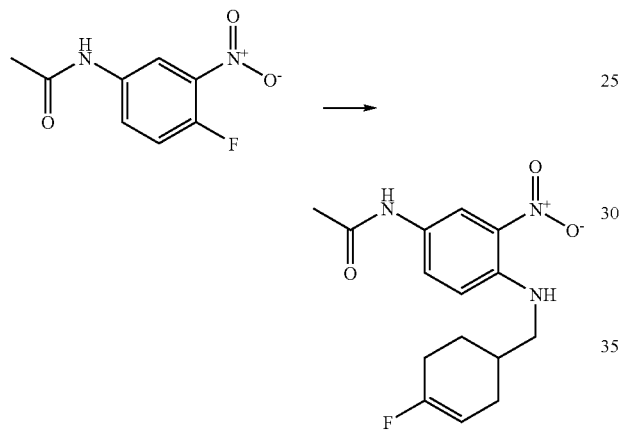

N-(4-Fluoro-3-nitrophenyl)acetamide (460 mg, 2.32 mmol) and [(4-fluorocyclohex-3-en-1-yl)methyl]amine hydrochloride (350 mg, 2.11 mmol) were stirred in 20 mL of EtOH containing TEA (0.735 mL, 5.28 mmol) at 75° C. for 48 h. The solvent was concentrated. The residue was dissolved in EtOAc and washed with aqueous 5% KHSO$_4$, saturated aqueous NaHCO$_3$ solution, brine and dried over anhydrous MgSO$_4$. The crude product was purified by silica gel flash chromatography using 2:1/hexanes:acetone as eluent. Yield: 553 mg (85%). $^1$H NMR (400 MHz, CHLOROFORM-D) δ 1.51-1.61 (m, 1 H), 1.84-1.93 (m, 1 H), 1.96-2.03 (m, 2 H), 2.16-2.18 (m, 3 H), 2.22-2.32 (m, 3 H), 3.26 (m, 2 H), 5.19 (m, 1 H), 6.84 (d, J=9.37 Hz, 1 H), 7.21 (s, 1 H), 7.79 (dd, J=9.18, 2.54 Hz, 1 H), 8.09 (d, J=2.54 Hz, 2 H).

Step D: N-(3-Amino-4-{[(4-fluorocyclohexyl)methyl]amino}phenyl)acetamide

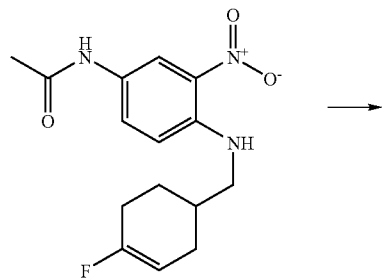

-continued

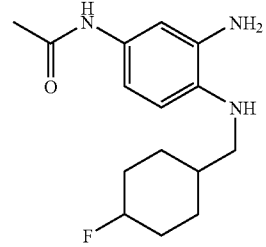

N-(4-{[(4-Fluorocyclohex-3-en-1-yl)methyl]amino}-3-nitrophenyl)acetamide (340 mg, 1.11 mmol) was dissolved in 25 mL of EtOAc containing a catalytic amount of 10% Pd/C. The solution was shaken under H$_2$ atmosphere (40 psi) using a Parr hydrogenation apparatus at rt for 48 h. The solution was filtered through celite and the solvent was evaporated. Yield: 308 mg (99%). MS (ESI) (M+H)$^+$ 279.95.

Step E: N-{2-tert-Butyl-1-[(4-fluorocyclohexyl)methyl]-1H-benzimidazol-5-yl}acetamide

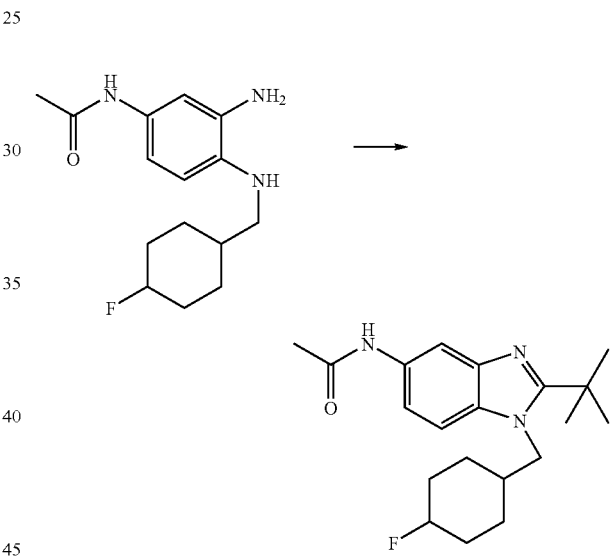

N-(3-Amino-4-{[(4-fluorocyclohexyl)methyl]amino}phenyl)acetamide (300 mg, 1.07 mmol) and DMAP (25 mg, 0.214 mmol) were dissolved in 10 mL of DCM. Trimethylacetyl chloride (0.145 mL, 1.18 mmol) was added dropwise and the solution was stirred at rt for 1 h. The solution was washed with aqueous NaHCO$_3$ solution, brine and dried over anhydrous MgSO$_4$. The residue was dissolved in 5 mL of AcOH and was heated at 150° C. for 2.5 h using a Personal Chemistry microwave apparatus. The solvent was evaporated. The residue was dissolved in EtOAc and washed with aqueous NaHCO$_3$ solution, brine and dried over anhydrous MgSO$_4$. The crude product was purified by silica gel flash chromatography using 2:1/acetone:hexanes as eluent. Yield: 196 mg (53%). $^1$HNMR (400 MHz, CHLOROFORM-D) δ 1.14-1.25 (m, 2 H), 1.37-1.45 (m, 1 H), 1.43-1.51 (m, 1 H), 1.54-1.57 (m, 9 H), 1.70-1.78 (m, 2 H), 1.70-1.77 (m, 1 H), 2.02-2.08 (m, 1 H), 2.10-2.17 (m, 1 H), 2.19-2.21 (m, 3 H), 4.12-4.19 (m, 2 H), 4.53 (m, 0.3 H), 4.73 (m, 0.3 H), 4.78 (m, 0.2 H), 4.90 (m, 0.2 H), 7.21-7.29 (m, 1 H), 7.30 (s, 1 H), 7.50-7.57 (m, 1 H), 7.64-7.67 (m, 1 H).

Step F: 2-tert-Butyl-1-[(4-fluorocyclohexyl)methyl]-1H-benzimidazol-5-amine

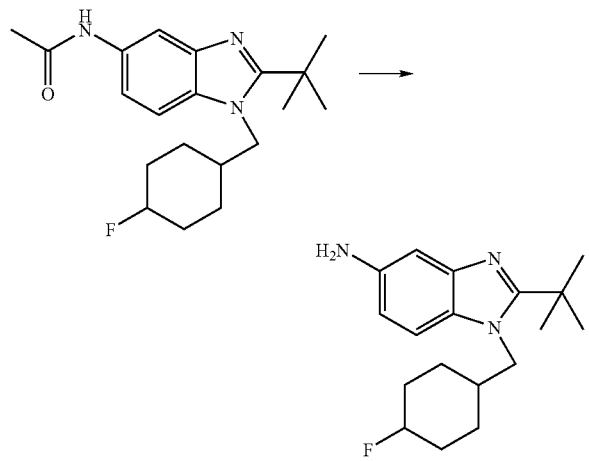

N-{2-tert-Butyl-1-[(4-fluorocyclohexyl)methyl]-1H-benzimidazol-5-yl}acetamide (190 mg, 0.550 mmol) was heated in 5 mL of 1:1/2M HCl:EtOH at 120° C. for 1 h using a Personal Chemistry microwaves apparatus. The solvent was evaporated. The residue was basified with 2M NaOH and extracted (3×) with EtOAc. The organic phase was washed with saturated aqueous NaCl solution and dried over anhydrous Na$_2$SO$_4$. The solvent was evaporated. Yield: 154 mg (92%). $^1$H NMR (400 MHz, METHANOL-D$_4$) δ 1.28-1.39 (m, 2 H), 1.41-1.50 (m, 1 H), 1.53-1.59 (m, 1 H), 1.61-1.64 (m, 9 H), 1.69 (d, J=7.81 Hz, 2 H), 1.95-2.03 (m, 0.7 H), 2.05-2.11 (m, 2 H), 2.13-2.22 (m, 0.3 H), 4.37-4.44 (m, 2.7 H), 4.47-4.56 (m, 0.3 H), 7.11 (t, J=2.05 Hz, 0.5 H) 7.13 (t, J=2.05 Hz, 0.5 H), 7.15-7.18 (m, 1 H), 7.67-7.73 (m, 1 H).

Example 25

N-{2-tert-Butyl-1-[(4-fluorocyclohexyl)methyl]-1H-benzimidazol-5-yl}cyclopropanesulfonamide

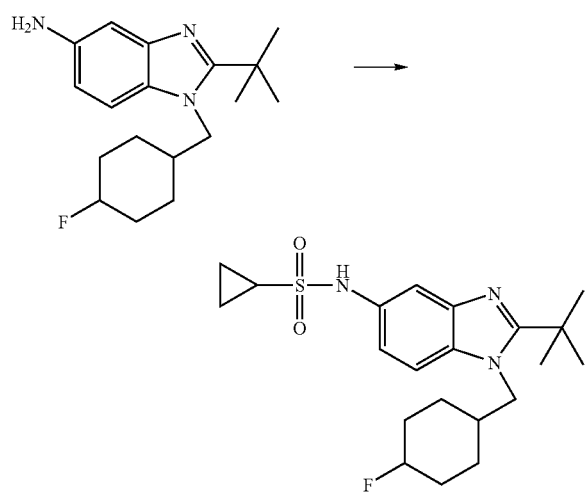

2-tert-Butyl-1-[(4-fluorocyclohexyl)methyl]-1H-benzimidazol-5-amine (56 mg, 0.199 mmol) and DMAP (25 mg, 0.199 mmol) were dissolved in 5 mL of DCM. Cyclopropanesulfonyl chloride (42 mg, 0.298 mmol) was added and the solution was stirred at rt for 3 h. The solution was washed with saturated aqueous NaHCO$_3$ solution, brine and dried over anhydrous MgSO$_4$. The solvent was evaporated and the product was purified by reversed-phase HPLC using 10-70% CH$_3$CN/H$_2$O and lyophilized affording the title compound as the corresponding TFA salt. Yield: 58 mg (56%). $^1$H NMR (400 MHz, METHANOL-D$_4$) δ 0.91-0.98 (m, 2 H), 1.03-1.09 (m, 2 H), 1.32-1.43 (m, 2 H), 1.45-1.52 (m, 1 H), 1.54-1.62 (m, 1 H), 1.64-1.67 (m, 9 H), 1.68-1.76 (m, 1 H), 1.97-2.05 (m, 1 H), 2.06-2.13 (m, 2 H), 2.54-2.62 (m, 1 H), 4.44-4.50 (m, 2 H), 4.53 (m, 0.5 H), 4.73 (m, 0.5 H), 7.43 (dd, J=9.08, 2.05 Hz, 1 H), 7.75 (d, J=1.95 Hz, 1 H), 7.83-7.89 (m, 1 H); MS (ESI) (M+H)$^+$ 408.0.

Example 26

N-{2-tert-Butyl-1-[(4-fluorocyclohexyl)methyl]-1H-benzimidazol-5-yl}-2-methylpropane-2-sulfonamide

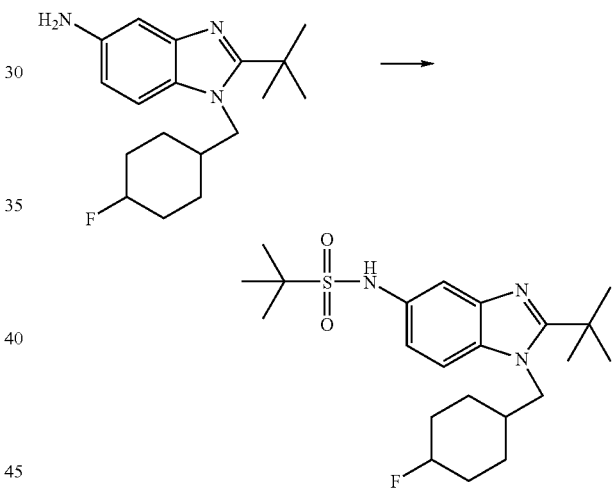

2-tert-Butyl-1-[(4-fluorocyclohexyl)methyl]-1H-benzimidazol-5-amine (53 mg, 0.175 mmol) and DMAP (21 mg, 0.175 mmol) were dissolved in 5 mL of DCM. t-Butylsulfinyl chloride (0.026 mL, 0.210 mmol) was added and the solution was stirred at rt for 1 h. The solution was washed with saturated aqueous NaHCO$_3$ solution, brine and dried over anhydrous MgSO$_4$. 3-Chloroperoxybenzoic acid (78 mg, 0.350 mmol) was added and the solution was stirred at rt for 2 h. The solution washed with saturated aqueous NaHCO$_3$ solution, brine and dried over anhydrous MgSO$_4$. The product was purified by reversed-phase HPLC using 10-70% CH$_3$CN/H$_2$O and lyophilized affording the title compound as the corresponding TFA salt. Yield: 47 mg (50%). $^1$H NMR (400 MHz, METHANOL-D$_4$) δ 1.36 (s, 9 H), 1.38-1.44 (m, 2 H), 1.44-1.51 (m, 1 H), 1.54-1.60 (m, 1 H), 1.63-1.66 (m, 9 H), 1.69-1.75 (m, 2 H), 1.96-2.04 (m, 1 H), 2.06-2.14 (m, 2 H), 4.42-4.48 (m, 2 H), 4.53 (m, 0.5 H), 4.72 (m, 0.5 H), 7.42 (dd, J=8.98, 2.15 Hz, 1 H), 7.79-7.86 (m, 2 H); MS (ESI) (M+H)$^+$ 424.0.

Example 27

N-{2-tert-butyl-1-[(4,4-difluorocyclohexyl)methyl]-1H-benzimidazol-5-yl}ethanesulfonamide

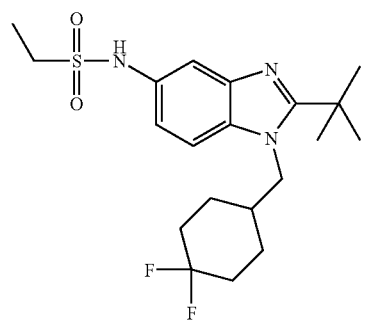

Step A. N-{2-tert-butyl-1-[(4,4-difluorocyclohexyl)methyl]-1H-benzimidazol-5-yl}ethanesulfonamide

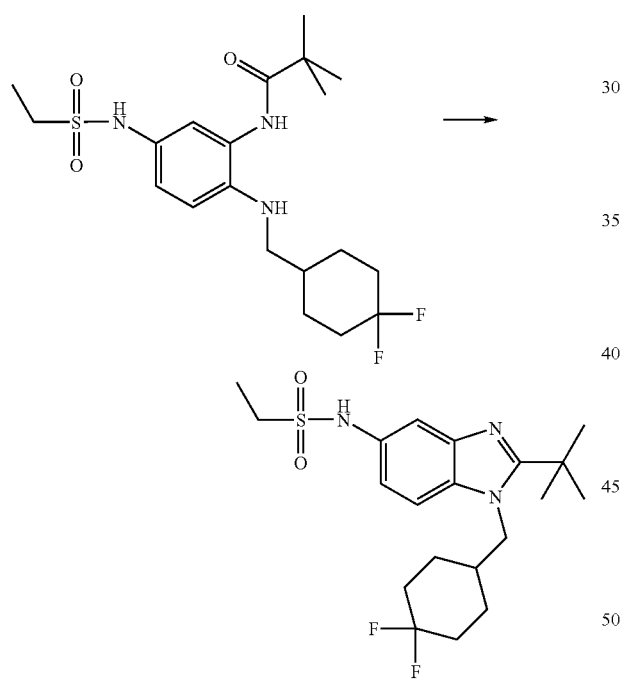

N-{2-{[(4,4-difluorocyclohexyl)methyl]amino}-5-[(ethylsulfonyl)amino]phenyl}-2,2-dimethylpropanamide (22.3 g, 0.051 mol) (for preparation, see the following steps B to E), PTSA*H₂O (10.8 g, 0.057 mol) and DMSO (100 mL) were mixed together and heated to 120° C. overnight. The room temperature cooled down reaction mixture was poured in cold water (600 mL). The product was extracted with DCM (5×200 mL).

The combined organic phases were washed with NaHCO₃ saturated solution (4×200 mL), brine and dried over anhydrous Na₂SO₄. The solvent was removed and the crude product was purified on silica gel (EtOAc:hexane 1:1) by flash chromatography (and treated with activated charcoal) to provide N-{2-tert-butyl-1-[(4,4-difluorocyclohexyl)methyl]-1H-benzimidazol-5-yl}ethanesulfonamide (18.4 g) as white solid.

Step B. N-(4-Fluoro-3-nitrophenyl)ethanesulfonamide

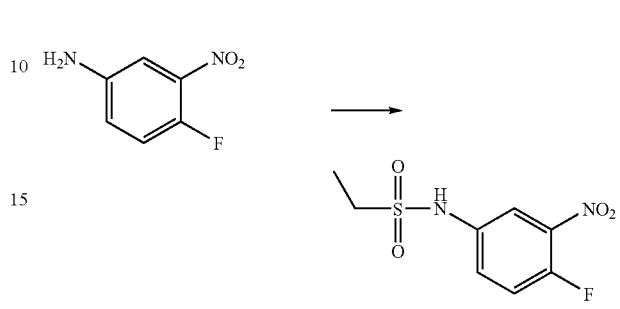

EtSO₂Cl (21.5 mL, 0.22 mol) was added drop wise to a mixture of 4-fluoro-3-nitroaniline (29.6 g, 0.19 mol) and pyridine (100 mL) at 0° C. The reaction mixture was allowed to warm to room temperature and stirred overnight. The reaction mixture was diluted with EtOAc (1 L). The resulting solution was washed with HCl 2N (4×200 mL), NaHCO₃ saturated solution (4×200 mL) and water (4×200 mL). The organic phase was dried over anhydrous Na₂SO₄ and the solvent was removed to provide the title product as beige solid (46.3 g)

Step C. N-(4-{[(4,4-Difluorocyclohexyl)methyl]amino}-3-nitrophenyl)ethanesulfonamide

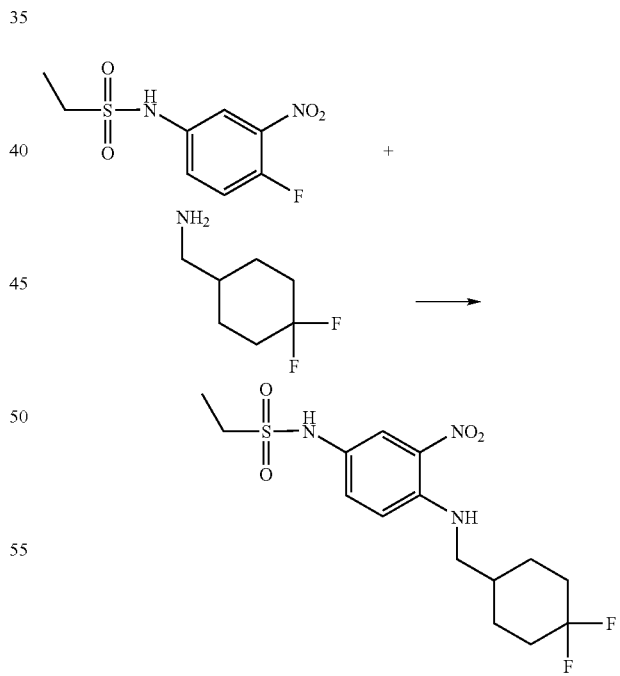

N-(4-Fluoro-3-nitrophenyl)ethanesulfonamide (26 g, 0.107 mol), [(4,4-difluorocyclohexyl)methyl]amine (approx. 15 g), DIPEA (20 mL) and DMSO (100 mL) were mixed together and heated to 65° C. overnight. Ethanolamine (5 g) was added and the reaction mixture was stirred until complete disappearance of N-(4-fluoro-3-nitrophenyl)ethanesulfonamide (approx. 4-5 hrs.). The room temperature cooled down reaction mixture was poured in cold water (900 mL). The product was extracted with DCM (5×200 mL). The combined organic phases were washed with HCl 2N (3×200 mL) and dried over anhydrous Na₂SO₄. The solvent was removed and the crude product was purified on silica gel by flash chromatography (this material can be re-crystallized using a mixture of EtOAc and hexane) to provide the title product (24.2 g) as orange solid.

Step D. N-(3-amino-4-{[(4,4-difluorocyclohexyl)methyl]amino}phenyl)ethanesulfonamide

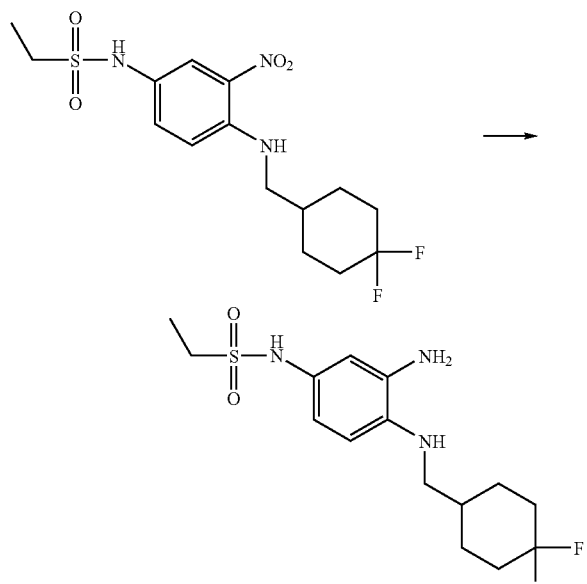

N-(4-{[(4,4-Difluorocyclohexyl)methyl]amino}-3-nitrophenyl)ethanesulfonamide (23.4 g) and Pd/C 10% in EtOAc (800 mL) were shaken together overnight under H₂ atmosphere (50 PSI) in a Parr hydrogenation apparatus. The reaction mixture was diluted with MeOH (400 mL) and filtered over celite bed. The solvent was removed to provide the desired title product (22.2 g) as beige solid.

Step E. N-{2-{[(4,4-difluorocyclohexyl)methyl]amino}-5-[(ethylsulfonyl)amino]phenyl}-2,2-dimethylpropanamide

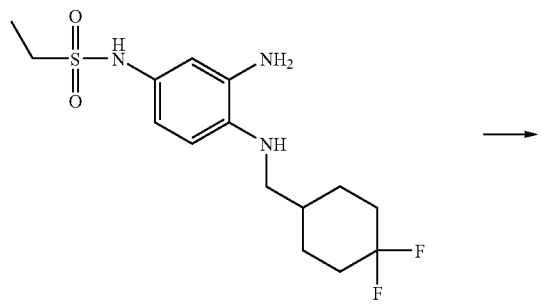

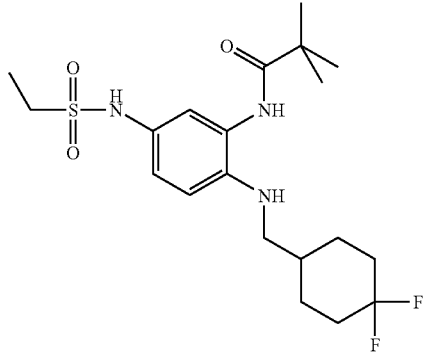

A solution of t-BuCOCl (7.6 g, 0.063 mol) in DCM (150 mL) was slowly added to a solution of N-(3-amino-4-{[(4,4-difluorocyclohexyl)methyl]amino}phenyl)ethanesulfonamide (22 g, 0.063 mol) and Et₃N (9.7 mL, 0.069 mol) in DCM (500 mL) at 0° C. The reaction mixture was stirred for 3 hrs. at 0° C. DCM (300 mL) and water (200 mL) were added. The organic layer was separated and washed with water (3×200 mL), brine and dried over anhydrous Na₂SO₄. The solvent was removed and the crude product was purified on silica gel by flash chromatography (EtOAc:hexane 1:1) to provide the title product (23.3 g) as beige solid.

Example 28

N-{2-tert-Butyl-1-[(4-fluorocyclohexyl)methyl]-1H-benzimidazol-5-yl}ethanesulfonamide (isomers)

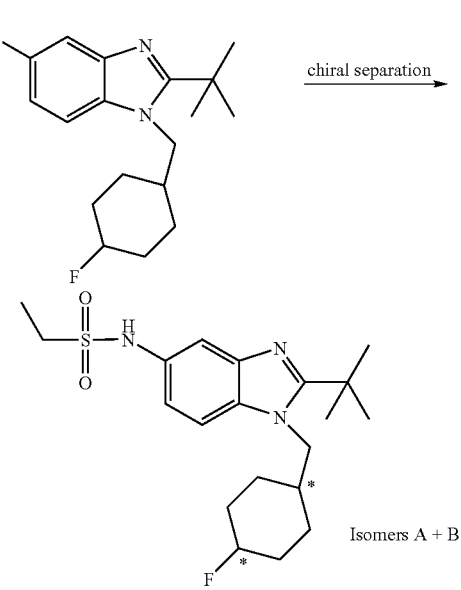

N-{2-tert-Butyl-1-[(4-fluorocyclohexyl)methyl]-1H-benzimidazol-5-yl}ethanesulfonamide (60 mg, TFA salt, 0.117 mmol) was separated on a chiral AD column using 10% EtOH/hexanes (0.1% diethylamine) giving respectively Isomer A (16 mg) and Isomer B (31 mg).

Isomer A: ¹H NMR (400 MHz, METHANOL-D4) δ 1.30 (t, J=7.42 Hz, 3 H), 1.41-1.52 (m, 3 H), 1.54-1.63 (m, 3 H), 1.65

(s, 9 H), 1.97-2.05 (m, 2 H), 2.15-2.24 (m, 1 H), 3.13 (q, J=7.29 Hz, 2 H), 4.47 (d, J=7.62 Hz, 2 H), 4.72 (s, 0.5 H), 4.85 (s, 0.5 H), 7.38 (dd, J=8.98, 2.15 Hz, 1 H), 7.73 (d, J=1.95 Hz, 1 H), 7.85 (d, J=8.98 Hz, 1 H); MS (ESI) (M+H)$^+$ 395.8; Chiral AD 15% EtOH/hexanes (0.1% DEA) k'=2.97.

Isomer B: $^1$H NMR (400 MHz, METHANOL-D4) δ 1.30 (t, J=7.32 Hz, 3 H), 1.34-1.39 (m, 2 H), 1.39-1.45 (m, 2 H), 1.65 (s, 9 H), 1.70-1.75 (m, 2 H), 2.06-2.13 (m, 3 H), 3.13 (q, J=7.42 Hz, 2 H), 4.37-4.43 (m, 0.5 H), 4.45 (d, J=7.62 Hz, 2 H), 4.49-4.56 (m, 0.5 H), 7.39 (dd, J=9.08, 2.05 Hz, 1 H), 7.73 (d, J=2.15 Hz, 1 H), 7.84 (d, J=9.18 Hz, 1 H); MS (ESI) (M+H)$^+$ 395.8; Anal. Calcd for $C_{20}H_{30}N_3O_2SF$+1.2+TFA+0.2 $H_2O$: C, 50.20; H, 5.94; N, 7.84. Found: C, 50.13; H, 5.81; N, 7.74; Chiral AD 15% EtOH/hexanes (0.1% DEA) k'=3.81.

| Isomer | Ki hCB1 (nM) | EC50 hCB1 (nM) | Emax hCB1 (%) | Sol. pH 7.4 (μM) | hClint (μL/min/mg) |
|---|---|---|---|---|---|
| A | 148 | — | — | 64 | — |
| B | 14.8 | 4.9 | 103 | 381 | 7.7 |

What is claimed is:

1. A compound selected from

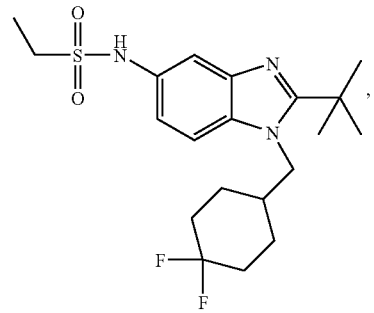

and pharmaceutically acceptable salts thereof.

2. A pharmaceutical composition comprising a compound according to claim 1 and a pharmaceutically acceptable carrier.

* * * * *